United States Patent [19]
Schriewer et al.

[11] Patent Number: 5,140,033
[45] Date of Patent: Aug. 18, 1992

[54] ANTIBACTERIAL 5-ALKYLQUINOLONECARBOXYLIC ACIDS

[75] Inventors: Michael Schriewer; Klaus Grohe; Andreas Krebs, all of Odenthal; Uwe Petersen, Leverkusen; Thomas Schenke, Gladbach; Ingo Haller, Wuppertal; Karl G. Metzger, Wuppertal; Rainer Endermann, Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 590,990

[22] Filed: Oct. 1, 1990

Related U.S. Application Data

[63] Continuation-in-part of Ser. No. 499,873, Mar. 27, 1990, now Defensive Publication No.

[30] Foreign Application Priority Data

Apr. 3, 1989 [DE] Fed. Rep. of Germany ....... 3910663

[51] Int. Cl.$^5$ ................. A61K 31/47; A61K 31/55; A61K 31/535; A61K 31/54
[52] U.S. Cl. ................. 514/312; 514/215; 514/216; 514/224.2; 514/230.5; 514/249; 514/300; 540/552; 540/556; 540/597; 544/48; 544/91; 544/105; 544/349; 546/15; 546/113; 546/156; 548/216; 548/218; 548/242; 548/300; 548/147; 548/409; 548/453; 548/541
[58] Field of Search ............ 546/113, 156, 94; 544/63, 91, 32, 101, 73; 514/300, 312, 230.5, 224.5, 230.2, 294

[56] References Cited

U.S. PATENT DOCUMENTS 4,638,067  1/1987  Culbertson et al. ............... 546/156
4,920,120  4/1990  Domagala et al. ................. 544/363
4,954,507  9/1990  Weber et al. ..................... 514/300
4,990,517  2/1991  Petersen et al. .................. 514/300

FOREIGN PATENT DOCUMENTS 276700   8/1988  European Pat. Off. .
343524  11/1989  European Pat. Off. ........... 546/156

OTHER PUBLICATIONS

Chiba et al., Chemical Abstracts, vol. 111, No. 153779 (1989).
Ziegler et al, J. Het. Chem. 25 p. 719 (1988).

Primary Examiner—Mukund J. Shah
Assistant Examiner—E. Bernhardt
Attorney, Agent, or Firm—Sprung Horn Kramer & Woods

[57] ABSTRACT

Antibacterial 5-alkylquinolonecarboxylic acids of the formula in which
$R^3$ is $C_1$-$C_4$-alkyl,
$R^1$ is optionally substituted alkyl or cycloalkyl, alkenyl, alkoxy, amino or alkylamino or optionally substituted phenyl,
$R^2$ is hydrogen or optionally substituted alkyl,
$R^4$ is a nitrogen-containing heterocyclic radical, and
A is hydrogen, halogen, methyl, cyano or nitro, or forms a bridge with $R^1$.

and hydrates and salts thereof.

3 Claims, No Drawings

ANTIBACTERIAL 5-ALKYLQUINOLONECARBOXYLIC ACIDS

This is a continuation-in-part of application Ser. No. 499,873, filed Mar. 27, 1990, now pending.

The invention relates to new quinolonecarboxylic acid derivatives which carry an alkyl, to processes for their preparation and to antibacterial agents and food additives containing them.

It has been found that quinolonecarboxylic acid derivatives of the formula (I)

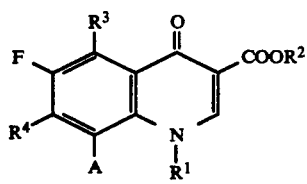

in which $R^1$ represents straight-chain or branched $C_1$–$C_4$-alkyl which is optionally substituted by hydroxyl, halogen, $C_1$–$C_3$-alkoxy or $C_1$–$C_3$-alkylthio, $C_3$–$C_6$-cycloalkyl which is optionally substituted by halogen or $C_1$–$C_3$-alkyl, $C_1$–$C_4$-alkenyl, and in addition $C_1$–$C_3$-alkoxy, amino, monoalkylamino having 1–3 C atoms, dialkylamino having 2–6 C atoms or phenyl which is optionally substituted by halogen, $R^2$ represents hydrogen, alkyl having 1 to 4 carbon atoms or (5-methyl-2-oxo-1,3-dioxol-4-yl)-methyl, $R^3$ denotes $C_1$–$C_4$-alkyl, $R^4$ represents a radical, which is optionally substituted in the ring system by hydroxyl or methyl, of the formula

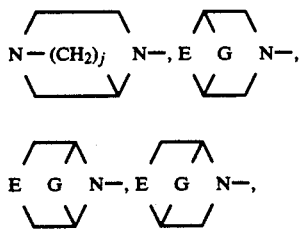

in which

E represents $R^5$—N, O or S,

G represents —(CH$_2$)$_j$—, CH$_2$—O—CH$_2$—, —CH$_2$—S—CH$_2$—, —CH$_2$—S— or

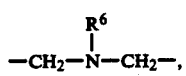

j represents 1, 2 or 3, $R^5$ represents hydrogen, alkyl, alkenyl or alkinyl having 1 to 4 carbon atoms which is optionally substituted by hydroxyl, benzyl which is optionally substituted by nitro or amino, oxoalkyl having 2 to 4 carbon atoms or (5-methyl-2-oxo-1,3-dioxol-4-yl)methyl, $R^6$ represents hydrogen or methyl, $R^4$ in addition represents a radical of the formula

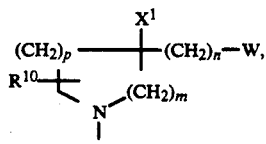

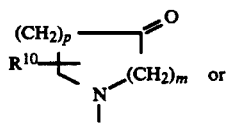

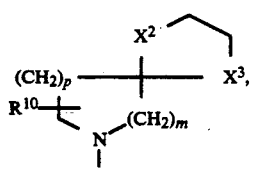

in which, p represents 0,1 or 2, m represents I or 2, where p+m together can be 1, 2 or 3, n represents 1 or 2, W represents

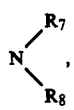

$OR^9$, $SR^9$, halogen or hydrogen, $X^1$ represents

$OR^9$, $SR^9$, halogen, CN, CONH$_2$ COOH or $C_1$–$C_4$-alkyl, $X^2$ and $X^3$ can be identical or different and represent oxygen or N—CH$_3$, $R^7$ represents hydrogen, $C_1$–$C_3$-alkyl, allyl or propargyl and $R^8$ represents hydrogen, $C_1$–$C_3$-alkyl or $C_3$–$C_6$-cycloalkyl, where $R^7$+$R^8$ together can also represent the groups —CH$_2$CH$_2$—O—CH$_2$CH$_2$— or —(CH$_2$)$_k$—, in which k can represent 3, 4 or 5, and $R^9$ represents hydrogen, $C_1$–$C_3$-alkyl or $C_1$–$C_3$-acyl, $R^{10}$ represents hydrogen or $C_1$–$C_3$-alkyl, $R^4$ also denotes a radical of the structure

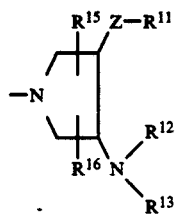

-continued

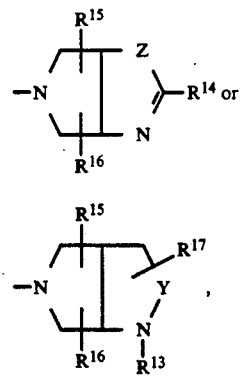

in which
R[11] can represent H, $C_1$–$C_3$-alkyl or $C_1$–$C_2$-acyl,
R[12] can represent H, $C_1$–$C_3$-alkyl, OH or $OCH_3$, where R[11] and R[12] together can also denote a $C_1$–$C_2$-alkylene bridge which is optionally monosubstituted or disubstituted by methyl,
R[13] can represent H, or $C_1$–$C_3$-alkyl, aryl, heteroaryl, benzyl, $C_1$–$C_4$-alkoxycarbony, $C_1$–$C_4$-acyl or (5-methyl-2-oxo-1,3-dioxol-4-yl)-methyl,
R[14] can represent H or $C_1$–$C_4$-alkyl,
R[15] can represent H or $CH_3$ or phenyl,
R[16] can represent H or $CH_3$ or phenyl,
R[17] can represent H or $CH_3$,
Y can represent O, $CH_2$, $CH_2CH_2$ or $CH_2$—O, where the linking of the $CH_2$—O group to the nitrogen can be both via O and via $CH_2$,
Z can represent O or S,
A represents hydrogen, halogen, methyl, cyano or nitro or, together with R[1], can also form a bridge of the structure

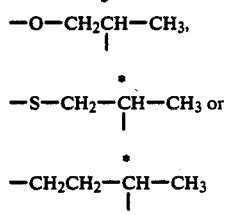

having the R- or S-configuration, and their pharmaceutically utilizable hydrates and acid addition salts and also the alkali metal, alkaline earth metal, silver and guanidinium salts of the carboxylic acids on which they are based, have a high antibacterial action, in particular in the gram-positive region.

They are therefore suitable as active compounds for human and veterinary medicine, where veterinary medicine also includes the treatment of fish for the therapy or prevention of bacterior infections.

Preferred compounds of the formula (I) are those in which
R[1] represents ethyl, isopropyl, cyclopropyl, vinyl, t-butyl, 2-hydroxyethyl, 2-fluoroethyl, amino, methylamino, phenyl, 4-fluorophenyl or 2,4-difluorophenyl,
R[2] represents hydrogen, alkyl having 1 to 3 carbon atoms or (5-methyl-2-oxo-1,3-dioxol-4-yl)-methyl,
R[3] represents $C_1$–$C_3$-alkyl, R[4] represents a substituted radical, which is optionally substituted in the ring system by methyl, of the formula

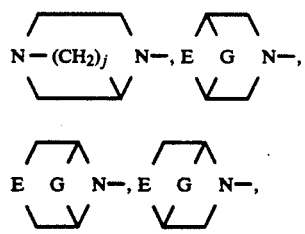

in which
E represents R[5]—N or O,
G represents —$(CH_2)_j$—, —$CH_2$—O—$CH_2$— or

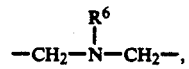

j represents 1, 2 or 3,
R[5] represents hydrogen, alkyl, alkenyl or alkinyl having 1 to 3 carbon atoms, which is optionally substituted by hydroxyl, benzyl which is optionally substituted by nitro or amino or oxoalkyl having 2 to 4 carbon atoms and
R[6] represents hydrogen or methyl,
R[4] in addition represents a radical of the formula

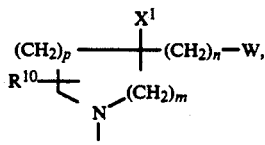

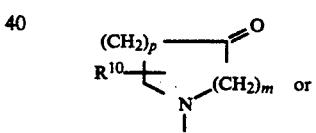

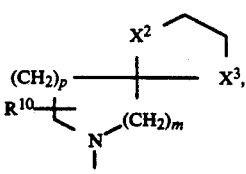

in which
p represents 0, 1 or 2,
m represents 1 or 2, where p+m together can be 1, 2 or 3,
n represents 1 or 2,
W represents

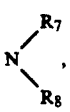

OR[9] or hydrogen,
X[1] represents

$OR^9$, fluorine, chlorine or $C_1$-$C_2$-alkyl, $X^2$ and $X^3$ can be identical or different and represent oxygen, sulphur or N—$CH_3$, $R^7$ represents hydrogen, $C_1$-$C_2$-alkyl or acetyl, $R^8$ represents hydrogen or $C_1$-$C_2$-alkyl, where $R^7+R^8$ together also denote the groups —$CH_2CH_2$—O—, —$CH_2CH_2$— or —$(CH_2)_k$—, in which k can represent 3, 4 or 5, $R^9$ represents hydrogen, $C_1$-$C_2$-alkyl or acetyl, $R^{10}$ represents hydrogen or $C_1$-$C_2$-alkyl, $R^4$ also represents a radical of the structure

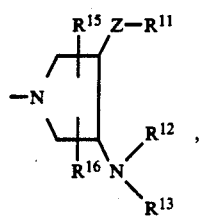

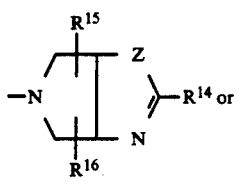

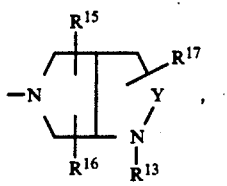

in which $R^{11}$ can represent H, $C_1$-$C_3$-alkyl or $C_1$-$C_2$-acyl, $R^{12}$ can represent H, $C_1$-$C_3$-alkyl, OH or $OCH_3$, where $R^{11}$ and $R^{12}$ together can also denote a $C_1$-$C_2$-alkylene bridge which is optionally monosubstituted or disubstituted by methyl, $R^{13}$ can represent H, $C_1$-$C_3$-alkyl, phenyl, benzyl, $C_1$-$C_4$-alkoxycarbonyl, $C_1$-$C_2$-acyl or (5-methyl-2-oxo-1,3-dioxol-4-yl)-methyl, $R^{14}$ can represent H or $C_1$-$C_2$-alkyl, $R^{15}$ can represent H or $CH_3$, $R^{16}$ can represent H or $CH_3$, $R^{17}$ can represent H or $CH_3$, Y can represent O, $CH_2$, $CH_2CH_2$ or $CH_2$—O, where the linking of the $CH_2$—O-group to the nitrogen can be both via O and via $CH_2$, Z can represent O, A represents H, fluorine, chlorine, methyl, cyano or nitro or together with $R^1$ can also form a bridge of the structure

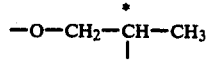

having the R- or S-configuration.

Particularly preferred compounds of the formula (I) are those in which $R^1$ represents ethyl, vinyl, t-butyl, cyclopropyl, 2-hydroxyethyl, 2-fluoroethyl, methylamino, 4-fluorophenyl or 2,4-difluorophenyl, $R^2$ represents hydrogen or alkyl having 1 to 2 carbon atoms, $R^3$ represents $C_1$-$C_3$-alkyl, $R^4$ represents a radical, which is optionally substituted in the ring system by methyl, of the formula

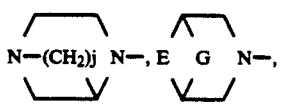

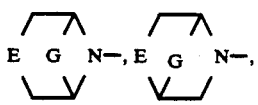

in which

E represents $R^5$—N,

G represents —$(CH_2)_j$—, j represents 1 or 2, $R^5$ represents hydrogen, alkyl, alkenyl or alkinyl having 1 to 3 carbon atoms and optionally substituted by hydroxyl, benzyl which is optionally substituted by nitro or amino, or oxoalkyl having 2 to 4 carbon atoms and $R^6$ represents hydrogen or methyl, $R^4$ in addition represents a radical of the formula

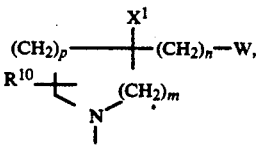

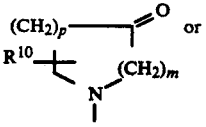

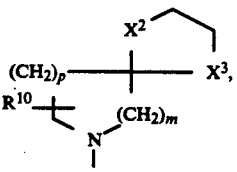

in which p represents 0, 1 or 2, m represents 1 or 2, where p+m together can be 1, 2 or 3, n represents 1, W represents

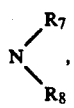

$OR^9$ or hydrogen,
$X^1$ represents

$OR^9$, chlorine or methyl, $X^2$ and $X^3$ can be identical or different and represent oxygen or $N-CH_3$, $R^7$ represents hydrogen or methyl,
$R^8$ represents hydrogen or methyl,
$R^9$ represents hydrogen or methyl,
$R^{10}$ represents hydrogen or methyl,
$R^4$ additionally denotes a radical of the structure

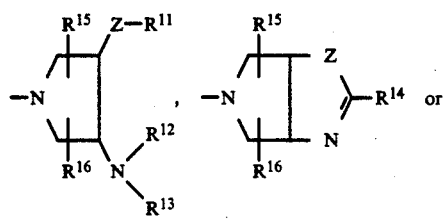

in which
$R^{11}$ can represent H, $C_1-C_2$-alkyl or acetyl,
$R^{12}$ can represent H or $C_1-C_2$-alkyl, where $R^{11}$ and $R^{12}$ together can also denote a $C_1-C_2$-alkylene bridge which is optionally substituted by methyl,
$R^{13}$ can represent H, $C_1C_2$-alkyl, hydroxyalky and as hydroxyethyl, benzyl, $C_1-C_4$-alkoxycarbonyl or $C_1-C_2$-acyl,
$R^{14}$ can represent H or $CH_3$,
$R^{15}$ can represent H or $CH_3$,
$R^{16}$ can represent H or $CH_3$,
$R^{17}$ can represent H or $CH_3$,
Y can represent O, $CH_2$, $CH_2CH_2$ or $CH_2-O$, where the linking of the $CH_2-O$-groups to the nitrogen can be both via O and via $CH_2$,
Z can represent O,
A represents H, fluorine or chlorine, or together with $R^1$ can also form a bridge of the structure

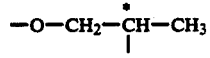

having the R- or S-configuration.

It has furthermore been found that the compounds of the formula (I) are obtained when compounds of the formula (II)

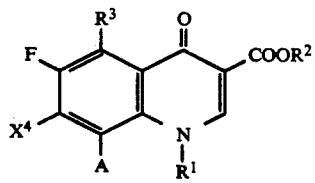

(II)

in which $R^1$, $R^2$, $R^3$ and A have the abovementioned meanings and $X^4$ represents halogen, in particular fluorine or chlorine, are reacted with compounds of the formula (III)

$$R^4-H \quad (III)$$

in which $R^4$ has the abovementioned meaning, if appropriate in the present of acid scavengers and if appropriate protective groups contained in $R^4$ are removed.

If, for example, 1-cyclopropyl-6,7,8-trifluoro-1,4-dihydro-5-methyl-4-oxo-3-quinolinecarboxylic acid and 1-methyl-octahydropyrrolo[3,4-b]pyridine are used as starting substances, the course of the reaction can be represented by the following equation:

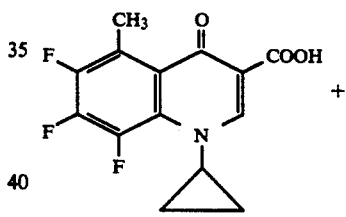

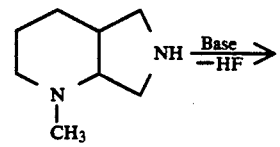

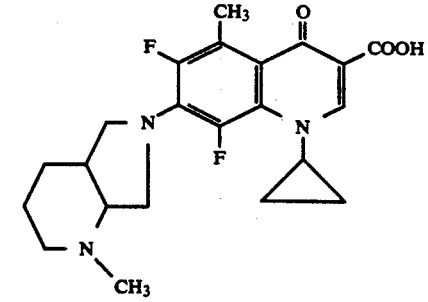

If, for example, 8-chloro-1-cyclopropyl-6,7-difluoro-1,4-dihydro-5-methyl-4-oxo-3-quinolinecarboxylic acid and 3-ethylaminomethyl-3-hydroxy-pyrrolidone are used as starting substances, then the course of the reaction can be represented by the following equation:

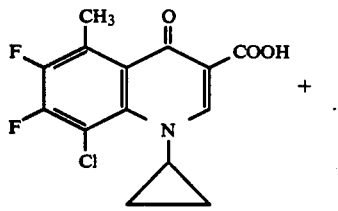

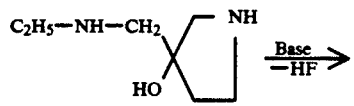

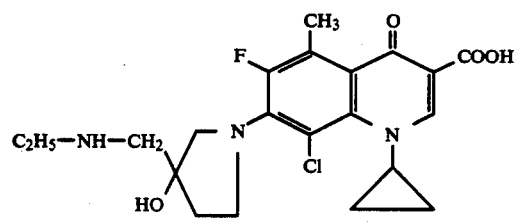

If, for example, 1-cyclopropyl-7-(2,7-diazabicylo[3.3.0]oct-7-yl)-6-fluoro-1,4-dihydro-5-methyl-4-oxo-3-quinolinecarboxylic acid and ethanol/hydrogen chloride are used as starting substances, then the course of the reaction can be represented by the following equation:

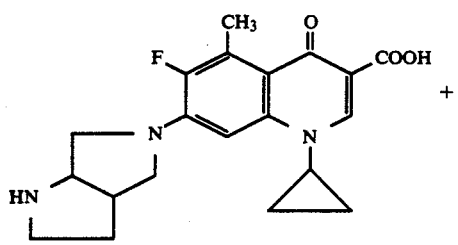

C₂H₅OH $\xrightarrow{HCl}$

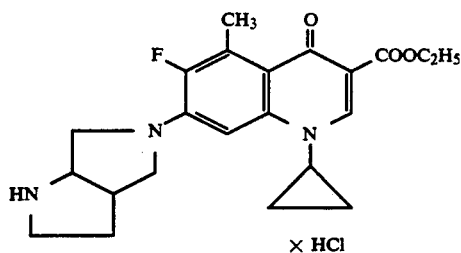

× HCl

The compounds of the formula II used as starting substances are known or can be prepared by known methods. Examples which may be mentioned are:

1-cyclopropyl-6,7,8-trifluoro-1,4-dihydro-5-methyl-4-oxo-3-quinolinecarboxylic acid,
8-chloro-1-cyclopropyl-6,7-difluoro-1,4-dihydro-5-methyl-4-oxo-3-quinolinecarboxylic acid,
1-cyclopropyl-6,7-difluoro-1,4-dihydro-5,8-dimethyl-4-oxo-3-quinolinecarboxylic acid,
1-ethyl-6,7,8-trifluoro-1,4-dihydro-5-methyl-4-oxo-3-quinolinecarboxylic acid
Ethyl 1-cyclopropyl-6,7,8-trifluoro-1,4-dihydro-5-methyl-4-oxo-3-quinolinecarboxylate,
Ethyl 8-chloro-1-cyclopropyl-6,7-difluoro-1,4-dihydro-5-methyl-4-oxo-3-quinolinecarboxylate,
6,7-difluoro-1-(4-fluoro-phenyl)-1,4-dihydro-5-methyl-4-oxo-3-quinolinecarboxylic acid,
6,7-difluoro-1-(2,4-difluoro-phenyl)-1,4-dihydro-5-methyl-4-oxo-3-quinolinecarboxylic acid.

7-Chloro-1-cyclopropyl-6,8-difluoro-1,4-dihydro-5-methyl-4-oxo-3-quinolinecarboxylic acid is not known. It can be prepared according to the following scheme.

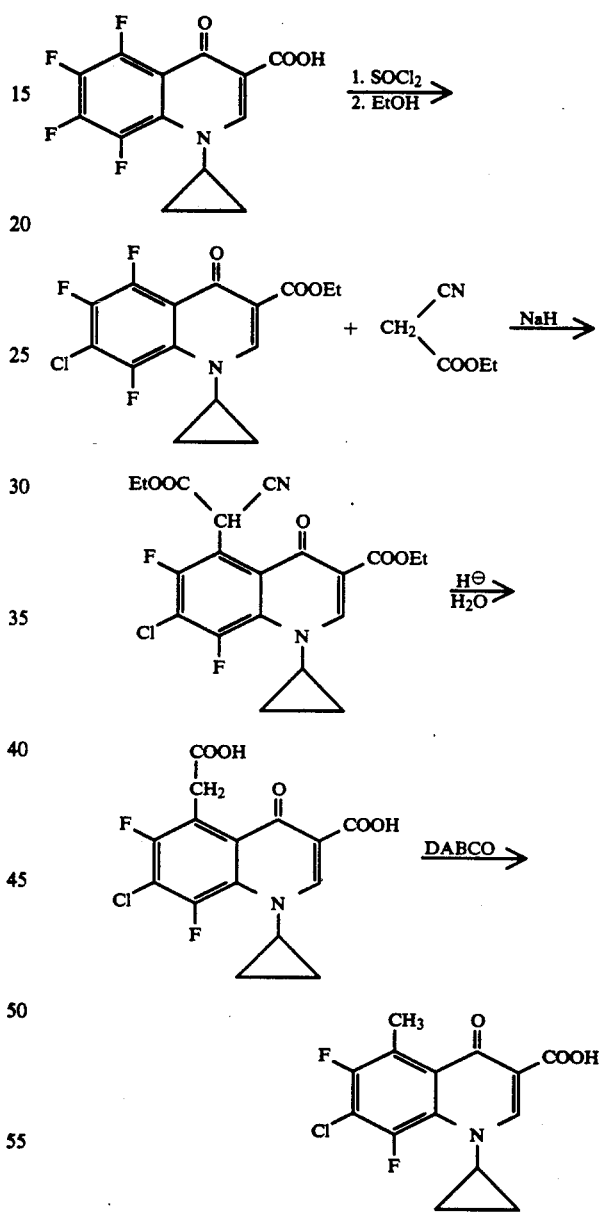

DABCO = 1,4-Diazabicylo[2,2,2]octane
The compounds of the formula III having the structures

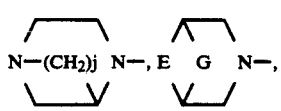

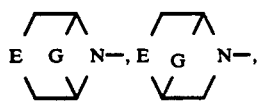

are known (EP-PS 230,274).

Some of the compounds of the formula III used as starting compounds and having the structures

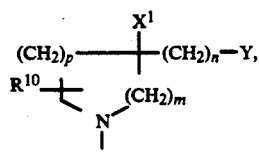

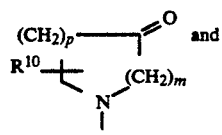

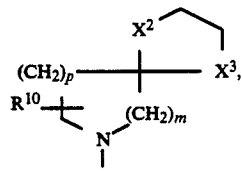

are new.

They can be prepared by various methods:

1. By reaction of the spiro-oxiranes protected on the nitrogen atom (1) [J. Med. Chem. 30, 222 (1987); U.S. Pat. No. 4,508,724; EP-PS 189,370] with amines (2), ring opening to give the hydroxylamines (3) occurs. Removal of the protective group yields starting compounds of the formula (IIIa):

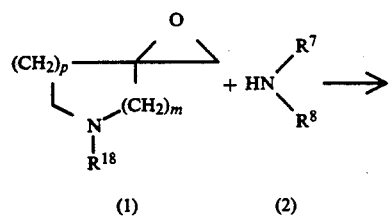

$R^{18}$ = COO-alkyl or $CH_2C_6H_5$

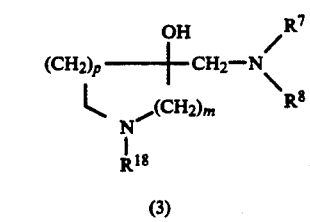

2. The cyclization of the succinic acid ester (4) Tetrahedron Letters 46, 4561 (1973)]with benzylamine yields the alkyl 1-benzyl-3-hydroxy-5-oxopyrrolidin-3-carboxylate (5) which, by reaction with an amine (2), reacts to give the amide (6). Subsequent reduction with LiAlH and hydrogenolytic cleavage of the benzyl group yields starting compounds of the formula (IIIb):

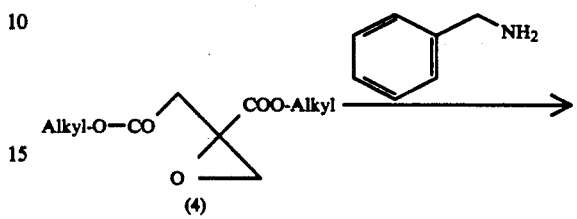

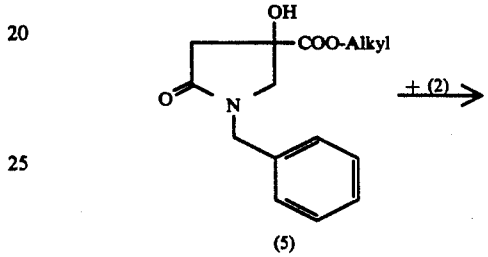

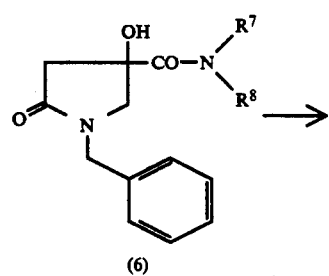

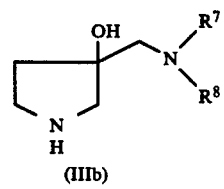

3. Reaction of (1-benzyl-3-hydroxy-2,5-dioxo-pyrrolidin-3-yl)-acetic acid (7) [Gazz. Chim. Ital. 24, 226 (1894)] to give the amide (8) and subsequent reduction with LiAlH4 and removal of the benzyl group yields starting compounds of the formula (IIIc):

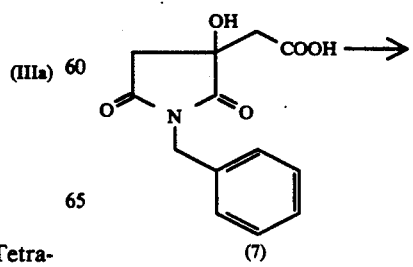

-continued

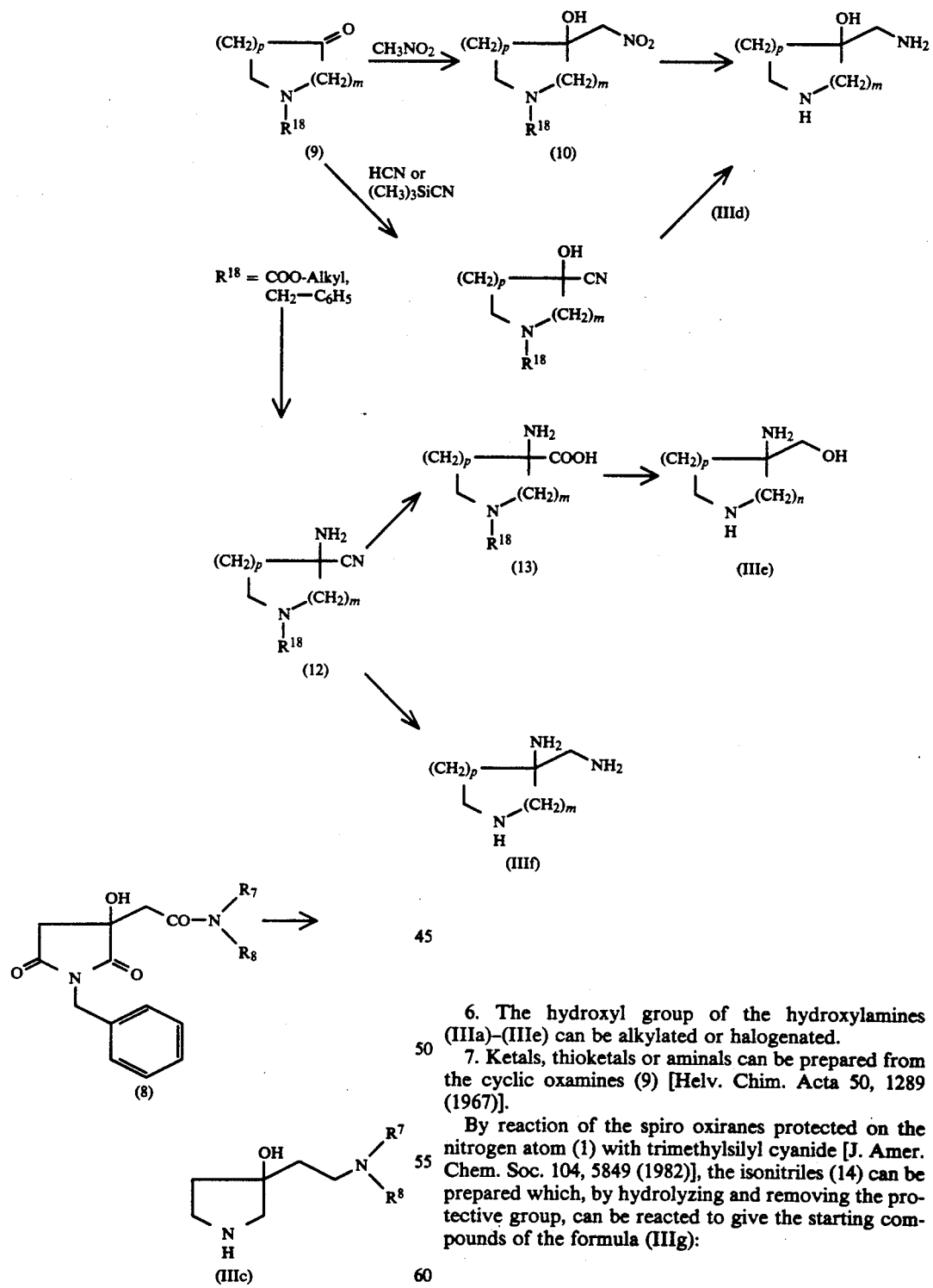

4. 3-Hydroxy-3-methyl-pyrrolidine can be prepared by LiAlH₄ reduction of 4-hydroxy-4-methyl-pyrrolidin-2-one [Zh. Org. Khim. 14, 7, p. 1420 (1978)] or by debenzylation of 1-benzyl-3-hydroxy-3-methylpyrrolidine (EP 132,845).

5. Starting from cyclic oxo-amines (9) which are blocked on the nitrogen by a protective group, starting compounds of the formulae (IIId), (IIIe), (IIIf), can be synthesized [Acta Chem. Scand. B 34, 319 (1980)].

6. The hydroxyl group of the hydroxylamines (IIIa)–(IIIe) can be alkylated or halogenated.

7. Ketals, thioketals or aminals can be prepared from the cyclic oxamines (9) [Helv. Chim. Acta 50, 1289 (1967)].

By reaction of the spiro oxiranes protected on the nitrogen atom (1) with trimethylsilyl cyanide [J. Amer. Chem. Soc. 104, 5849 (1982)], the isonitriles (14) can be prepared which, by hydrolyzing and removing the protective group, can be reacted to give the starting compounds of the formula (IIIg):

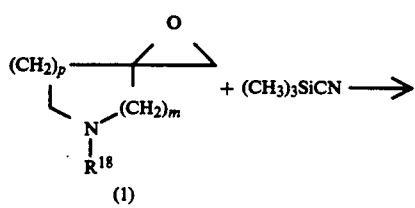

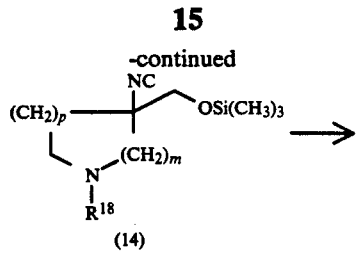

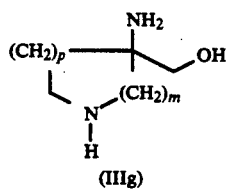

Examples of starting compounds of the formula (III) which may be mentioned are the following compounds, it being possible to employ chiral compounds both as racemates and as enantiomerically pure substances:
3-Aminomethyl-3-hydroxy-pyrrolidine,
3-Acetylaminomethyl-3-hydroxy-pyrrolidine,
3-tert.-Butoxycarbonylaminomethyl-3-hydroxy-pyrrolidine,
3-Hydroxy-3-methylaminomethyl-pyrrolidine,
3-Ethylaminomethyl-3-hydroxy-pyrrolidine,
3-Hydroxy-3-propylaminomethyl-pyrrolidine,
3-Ethylaminomethyl-3-methoxy-pyrrolidine,
3-Ethoxy-3-ethylaminomethyl-pyrrolidine,
3-Chloro-3-ethylaminomethyl-pyrrolidine,
3-Ethylaminomethyl-3-fluoro-pyrrolidine,
3-Ethylaminomethyl-3-methyl-pyrrolidine,
3-Ethylaminomethyl-3-mercapto-pyrrolidine,
3-Ethylaminomethyl-3-methylthio-pyrrolidine,
3-Acetoxy-3-ethylaminomethyl-pyrrolidine,
3-Dimethylaminomethyl-3-hydroxy-pyrrolidine,
3-Hydroxy-3-pyrrolidinomethyl-pyrrolidine,
3-Hydroxy-3-morpholinomethyl-pyrrolidine,
3-Amino-3-ethylaminomethyl-pyrrolidine,
3-Acetylamino-3-ethylaminomethyl-pyrrolidine,
3-Ethylaminomethyl-3-methylamino-pyrrolidine,
3-Dimethylamino-3-ethylaminomethyl-pyrrolidine,
3-Amino-3-hydroxymethyl-pyrrolidine,
3-Acetylamino-3-hydroxymethyl-pyrrolidine,
3-Amino-3-methoxymethyl-pyrrolidine,
3-tert.-Butoxycarbonylamino-3-methoxymethyl-pyrrolidine,
3-Amino-3-methylthiomethyl-pyrrolidine,
3-Amino-3-mercaptomethyl-pyrrolidine,
3-Cyclopropylaminomethyl-3-hydroxy-pyrrolidine,
3-Isopropylaminomethyl-3-hyiroxy-pyrrolidine,
1,4-Dioxa-7-azaspiro[4,4]nonane,
1-Oxa-4,7-diazaspiro[4,4]nonane,
4-Methyl-1-oxa-4,7-diazaspiro[4,4]nonane,
1-Thia-4,7-diazaspiro[4,4]nonane,
1,4,7-Triazaspiro[4,4]nonane,
1,4-Dimethyl-1,4,7-triazaspiro[4,4]nonane.

Some of the compounds of the formula III used as a starting material and having the structures

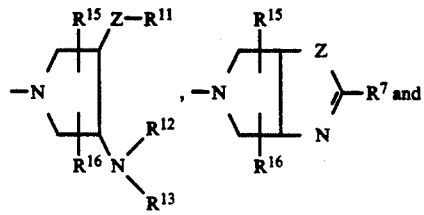

are also new. They can be prepared by the following methods:

1. Starting from the N-protected 3,4-epoxypyrrolidine (1) (German Offenlegungsschrift 1,929,237, U.S. Pat. No. 4,254,135), which can optionally carry a further one or two methyl or phenyl radicals, the starting compounds of the formula (IIIa)–(IIIe) are prepared.

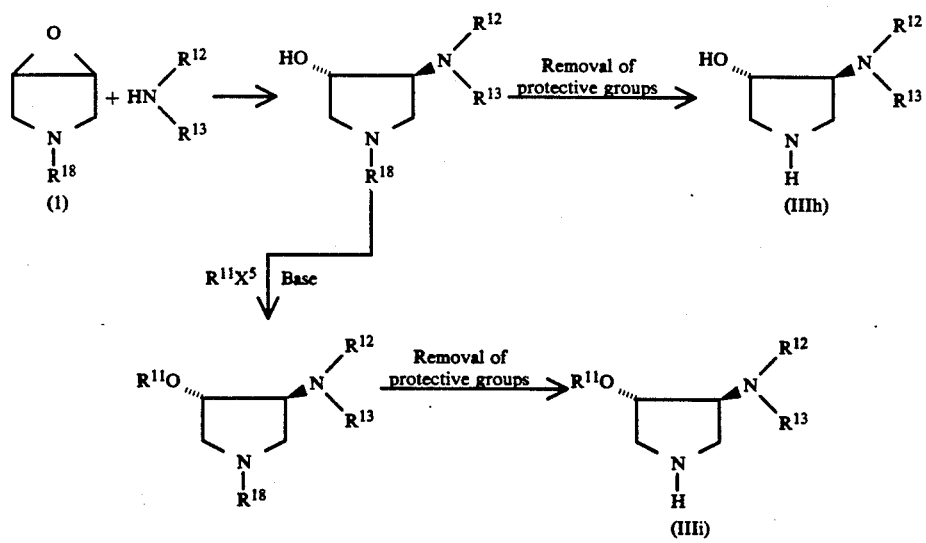

$R^{18}$=benzyl, acyl, alkoxycarbonyl, benzyloxycarbonyl, trialkylsilyl or sulphonyl (examples of protective groups), X=leaving group such as halogen, alkyl- or arylsulphonyloxy

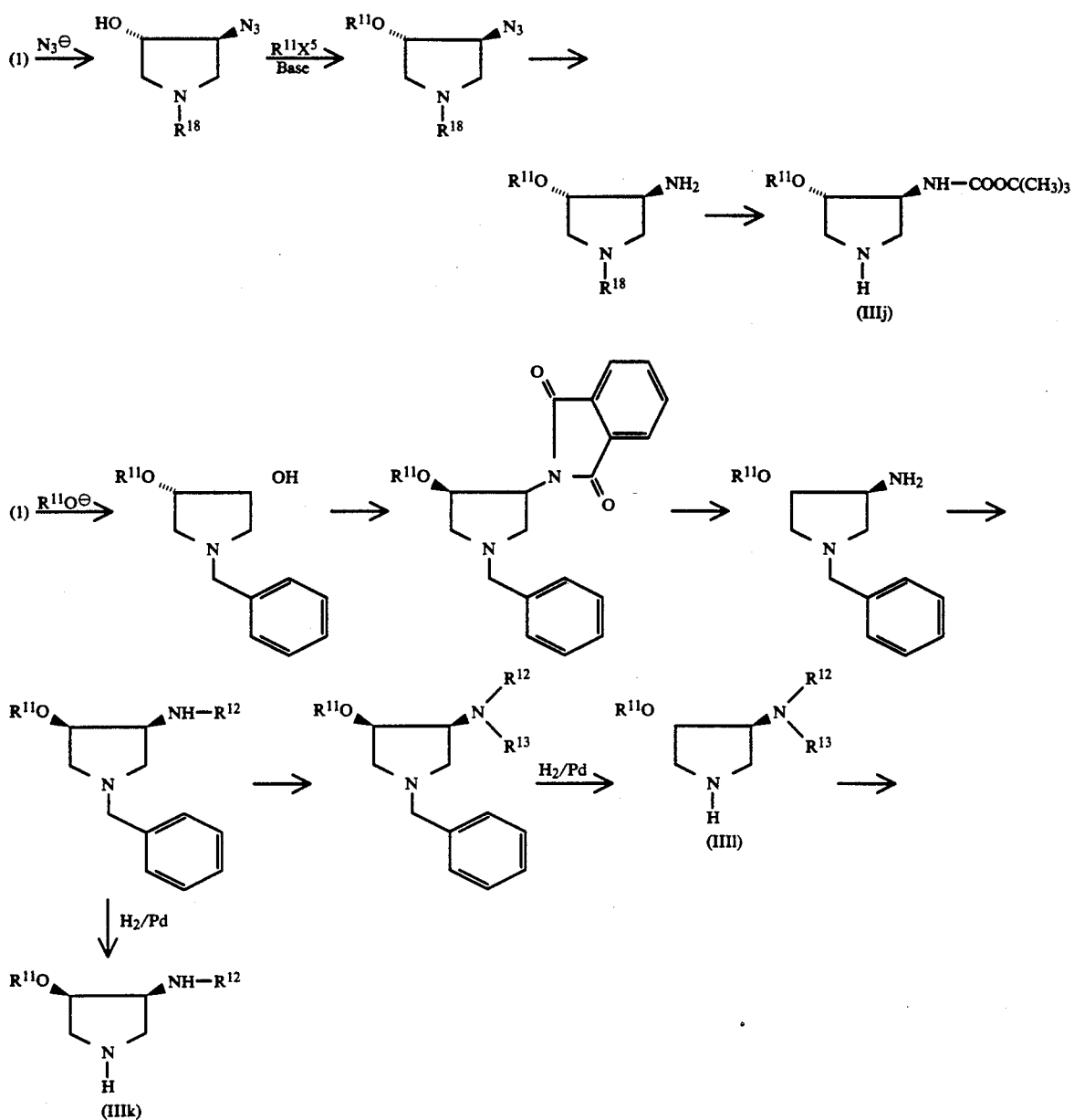
2. Starting compounds of the formula (IIIm) are obtained from 2-(1,2-dichloroethyl)-oxirane via the following reaction sequence:
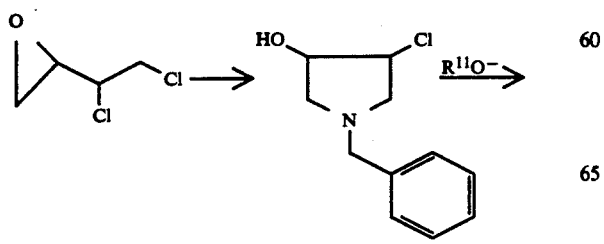
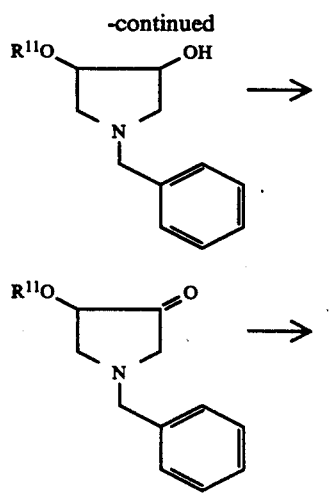

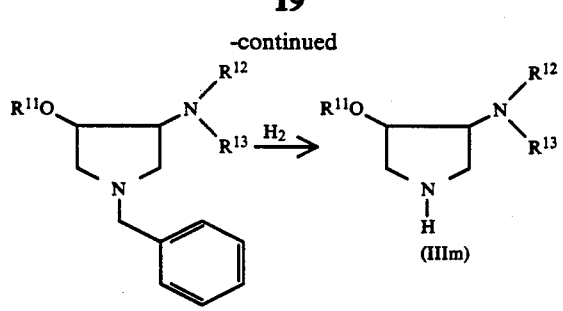

3. By addition of azides to N-benzylmaleimides optionally substituted with one or two methyl or phenyl radicals, starting compounds of the formula (IIIn) can be prepared:

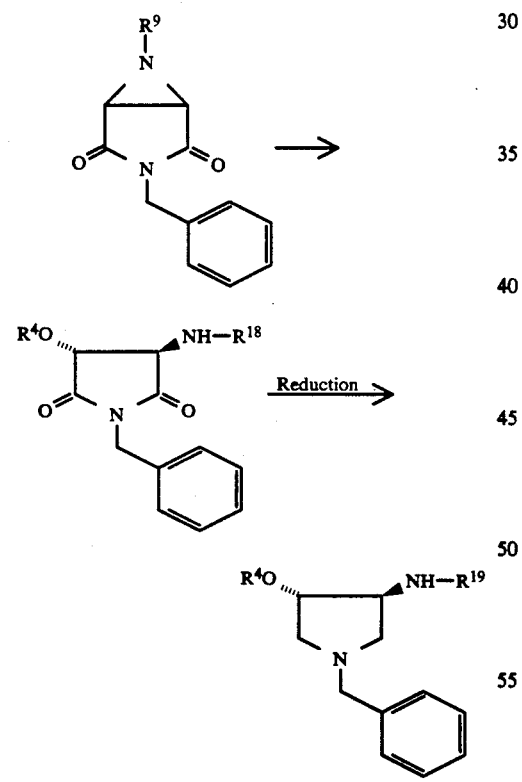

$R^{19}$=H, alkyl or benzyl.

4. From the 3,4-epoxypyrrolidines (1) via a cyclization with thionyl chloride, the starting compounds of the formula (IIIo) are obtained:

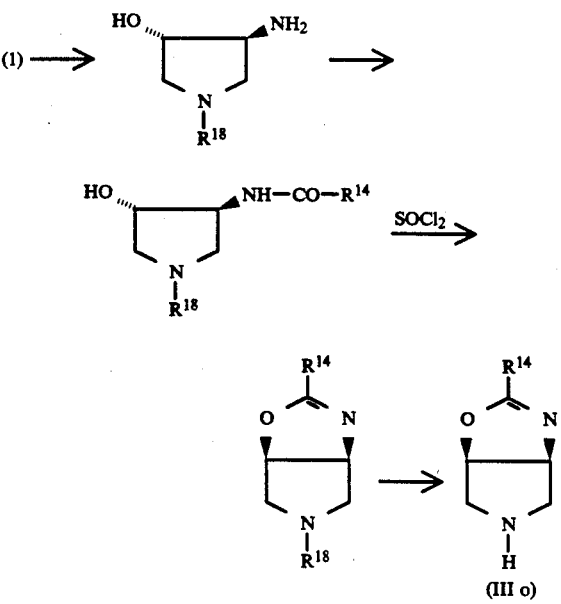

5. By reacting the 3,4-epoxypyrrolidines (1) with ethanolamines by intramolecular etherification, the starting compounds of the formula (IIIp) are obtained:

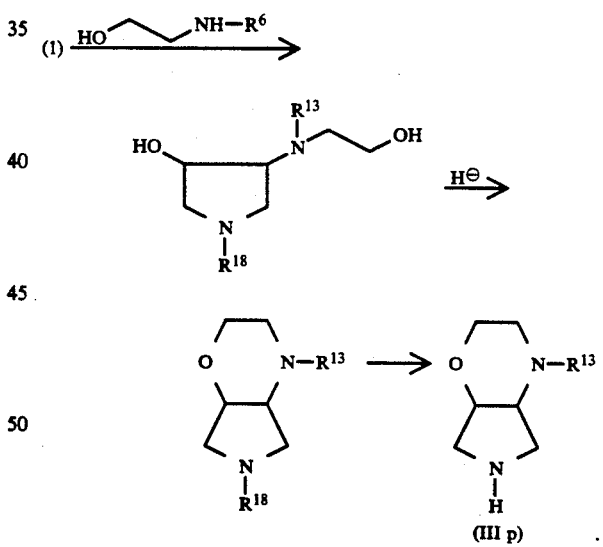

6. The starting compounds of the formula (IIIq) are obtained from amino acetaldehyde dimethyl acetal via an intramolecular 1,3-dipolar cycloaddition.

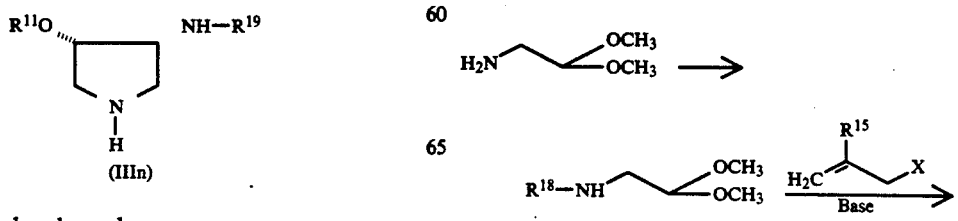

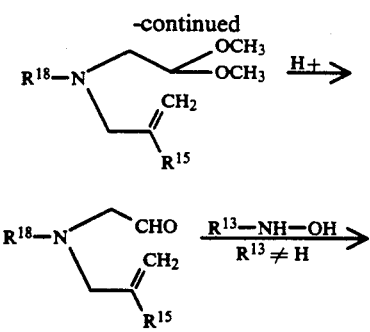
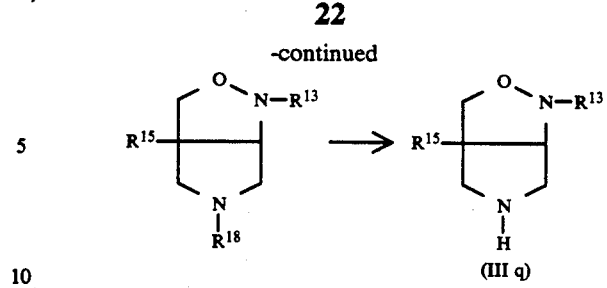
7. Starting from N-benzyl-pyridine-2,3-dicarboximide, starting compounds (IIIr) or (IIIl) are prepared via the reaction steps indicated.
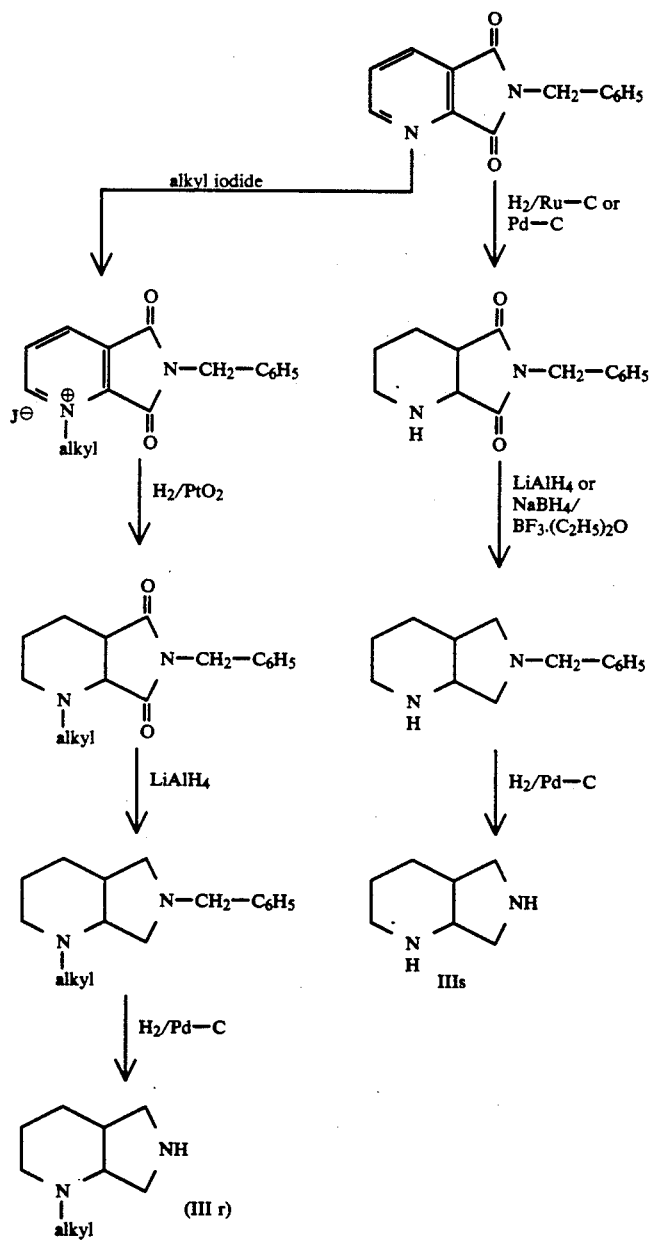
8. N-benzyl-maleimide adds 2-chloroethylamine to give the 3-(2-chloroethylamino)-succinimides, which are reacted to give the starting compounds of the formula (IIIt):

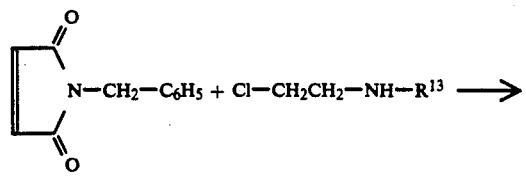

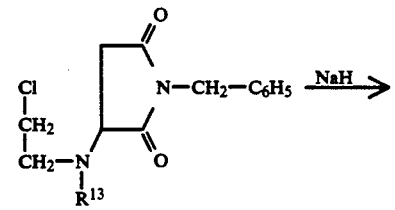

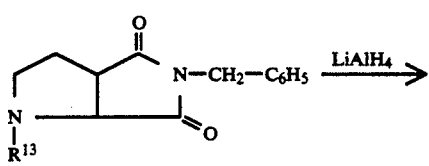

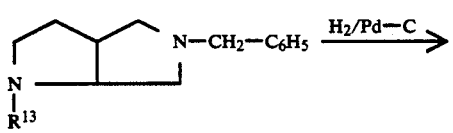

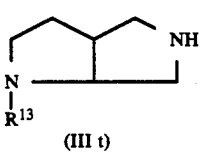

(III t)

9. 2-Methyl-2-propenal dimethylhydrazone reacts with N-benzylmaleimide to give a cycloadduct which can be converted into the starting compound (IIIu) by the reaction sequence indicated.

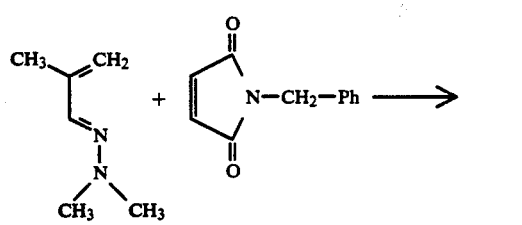

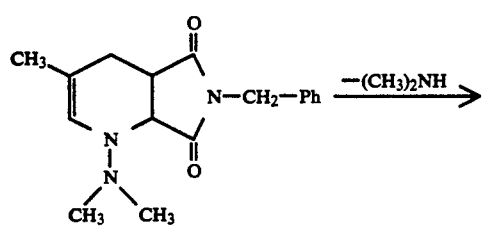

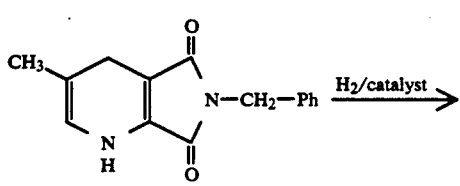

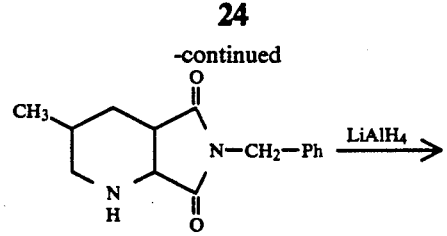

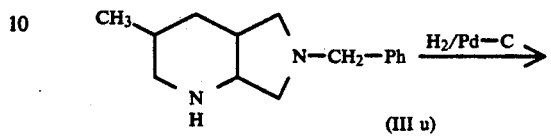

(III u)

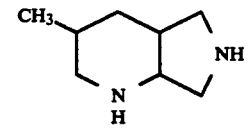

According to this general reaction scheme, for example, the following starting compounds can be prepared. The can be prepared and employed as diastereomer mixtures, in diastereomerically pure and also in enantiomerically pure form.

4-Amino-3-hydroxypyrrolidine,
3-Hydroxy-4-methylaminopyrrolidine,
4-Dimethylamino-3-hydroxypyrrolidine,
4-Ethylamino-3-hydroxypyrrolidine,
3-Amino-4-methoxypyrrolidine,
4-Methoxy-3-methylaminopyrrolidine,
3-Dimethylamino-4-methoxypyrrolidine,
3-Ethylamino-4-methoxypyrrolidine,
3-Amino-4-ethoxypyrrolidine,
4-Ethoxy-3-methylaminopyrrolidine,
3-Dimethylamino-4-ethoxypyrrolidine,
4-Ethoxy-3-ethylaminopyrrolidine,
3-Hydroxy-4-hydroxyaminopyrrolidine,
3-Hydroxy-4-methoxyaminopyrrolidine,
3-Hydroxyamino-4-methoxypyrrolidine,
4-Methoxy-3-methoxyaminopyrrolidine,
3-Benzylamino-4-methoxypyrrolidine,
4-Methoxy-3-((5-methyl-2-oxo-1,3-dioxol-4-yl)-methylamino)pyrrolidine,
3-Amino-4-methylmercaptopyrrolidine,
3-Acetoxy-4-dimethylaminopyrrolidine,
3-Acetamido-4-methoxypyrrolidine,
4-Methoxy-3-methoxycarbonylaminopyrrolidine,
3-Formamido-4-methoxylpyrrolidine,
3-Amino-4-methoxy-2-methylpyrrolidine,
3-Amino-4-methoxy-5-methylpyrrolidine,
4-Methoxy-2-methyl-3-methylaminopyrrolidine,
4-Methoxy-5-methyl-3-methylaminopyrrolidine,
3-Amino-4-methoxy-2-phenylpyrrolidine,
4-Methoxy-3-methylamino-5-phenylpyrrolidine,
3-Methyl-2,7-diazabicyclo[3.3.0]octane,
4-Methyl-2,7-diazabicyclo[3.3.0]octane,
5-Methyl-2,7-diazabicyclo[3.3.0]octane,
3,5-Dimethyl-2,7-diazabicyclo[3.3.0]octane,
1,5-Dimethyl-2,7-diazabicyclo[3.3.0]octane,
2-Oxa-4,7-diazabicyclo[3.3.0]octane,
3,3-Dimethyl-2-oxa-4,7-diazabicyclo[3.3.0]octane,
2-Oxa-2,7-diazabicyclo[3.3.0]octane,
1,2-Dimethyl-3-oxa-2,7-diazabicyclo[3.3.0]octane,
2,5-Dimethyl-3-oxa-2,7-diazabicyclo[3.3.0]octane,
2,8-Dimethyl-3-oxa-2,7-diazabicyclo[3.3.0]octane,
5-Methyl-3-oxa-2,7-diazabicyclo[3.3.0]octane, 2-Oxa-4,7-diazabicyclo[3,3,0]oct-3-ene,
3-Methyl-2-oxa-4,7-diazabicyclo[3.3.0]oct-3-ene,
3-Phenyl-2-oxa-4,7-diazabicyclo[3.3.0]oct-3-ene,
6-Methyl-2-oxa-4,7-diazabicyclo[3.3.0]oct-3-ene,
8-Methyl-2-oxa-4,7-diazabicyclo[3.3.0]oct-3-ene,
3-Methyl-2,8-diazabicyclo[4.3.0]nonane,
4-Methyl-2,8-diazabicyclo[4.3.0]nonane,
5-Methyl-2,8-diazabicyclo[4.3.0]nonane,
6-Methyl-2,8-diazabicyclo[4.3.0]nonane,
3-Methyl-2-oxa-5,8-diazabicyclo[4.3.0]nonane,
4-Methyl-2-oxa-5,8-diazabicyclo[4.3.0]nonane,
1-Methyl-2-oxa-5,8-diazabicyclo[4.3.0]nonane,
3,5-Dimethyl-2-oxa-5,8-diazabicyclo[4.3.0]nonane,
2-Thia-5,8-diazabicyclo[4.3.0]nonane,
5-Methyl-2-thia-5,8-diazabicyclo[4.3.0]nonane,
3,5-Dimethyl-2-thia-5,8-diazabicyclo[4.3.0]nonane,
3-Oxa-2,8-diazabicyclo[4.3.0]nonane,
2-Methyl-9-oxa-2,8-diazabicyclo[4.3.0]nonane,
4-Methyl-3-oxa-2,8-diazabicyclo[4.3.0]nonane,
2,5-Dimethyl-3-oxa-2,8-diazabicyclo[4.3.0]nonane,
3-Oxa-5,8-diazabicyclo[4.3.0]nonane,
5-Methyl-3-oxa-5,8-diazabicyclo[4.3.0]nonane,
1,5-Dimethyl-3-oxa-5,8-diazabicyclo[4.3.0]nonane,
4,4-Dimethyl-3-oxa-5,8-diazabicyclo[4.3.0]nonane.

The reaction of (II) with (III), in which the compounds (III) can also be employed in the form of their hydrochlorides, is preferably carried out in a diluent such as dimethyl sulphoxide, N,N-dimethylformamide, N-methylpyrrolidone, hexamethylphosphoramide, sulpholane, acetonitrile, water, an alcohol such as methanol, ethanol, n-propanol or isopropanol, glycol monomethyl ether or pyridine. Mixtures of these diluents can also be used.

Acid scavengers which can be used are all customary inorganic and organic acid-binding agents. These preferably include the alkali metal hydroxides, alkali metal carbonates, organic amines and amidines. Those which may be mentioned as being particularly suitable are: triethylamine, 1,4-diazabicyclo[2.2.2]octane(DABCO),1,8-diazabicyclo[5.4.0]undec-7-ene (DBU) or excess amine (III).

The reaction temperatures can be varied within a relatively wide range. In general, the reaction is carried out between about 20° and 200° C., preferably between 80° and 180° C.

The reaction can be carried out at normal pressure, but also at elevated pressure. In general, the reaction is carried out at pressures between about 1 and 100 bar, preferably between 1 and 10 bar.

When carrying out the process according to the invention, 1 to 15 moles, preferably 1 to 6 moles, of the compound (111) are employed per mole of the carboxylic acid (II).

Free hydroxyl groups can be protected during the reaction by a suitable hydroxyl protective group, for example by the tetrahydropyranyl radical, and after completion of the reaction are set free again (see J.F.W. McOmie, Protective Groups in Organic Chemistry (1973), page 104).

Free amino functions can be protected during the reaction by a suitable amino protective group, for example by the ethoxycarbonyl or the tert.-butoxycarbonyl radical, and after completion of the reaction are released again by treatment with a suitable acid such as hydrochloric acid or trifluoroacetic acid (see Houben-Weyl, Methoden der organischen Chemie [Methods of Organic Chemistry], volume E4, page 144 (1983); J.F.W. McOmie, Protective Groups in Organic Chemistry (1973), page 43).

To prepare the ester according to the invention, the carboxylic acid on which they are based is preferably reacted in excess alcohol in the presence of strong acids, such as sulphuric acid, anhydrous hydrogen chloride, methanesulphonic acid, p-toluenesulphonic acid or acidic ion exchangers, at temperatures from about 20° to 200° C., preferably about 60° to 120° C. The resultant water of reaction can also be removed by azeotropic distillation using chloroform, tetrachloromethane, benzene or toluene.

The preparation of esters is also advantageously carried out by heating the acid on which they are based with dimethylformamide dialkyl acetal in a solvent such as dimethylformamide.

The (5-methyl-2-oxo-1,3-dioxol-4-yl)-methyl esters used as a prodrug are obtained by reaction of an alkali metal salt of the carboxylic acid on which they are based with 4-bromomethyl or 4-chloromethyl-5-methyl-1,3-dioxol-2-one in a solvent such as dimethylformamide, dimethylacetamide, N-methylpyrrolidone, dimethyl sulphoxide or tetramethylurea at temperatures from about 0° to 100° C., preferably 0° to 50° C.

The preparation of the acid addition salts of the compounds according to the invention is carried out in a customary manner, for example by dissolving the betaine in excess aqueous acid and precipitating the salt with a water-miscible organic solvent such as methanol, ethanol, acetone or acetonitrile. Equivalent amounts of betaine and acid can also be heated in water or an alcohol such as glycol monomethyl ether and then evaporated to dryness or the precipitated salt filtered off with suction. Pharmaceutically utilizable salts are taken to mean, for example, the salt of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal or alkaline earth metal salts of the carboxylic acids according to the invention are obtained, for example, by dissolving the betaine in a subequivalent amount of alkali metal or alkaline earth metal hydroxide solution, filtering off undissolved betaine and evaporating the filtrate to dryness. Pharmaceutically suitable salts are those of sodium, potassium or calcium. The corresponding silver salts are obtained by reaction of an alkali metal salt or alkaline earth metal salt with a suitable silver salt such as silver nitrate.

In addition to the active compounds mentioned in the examples, the compounds shown by way of example in Table 1 can also be prepared, it being possible for these compounds to be present both as diastereomer mixtures and also as diastereomerically pure or enantiomerically pure compounds.

The compounds according to the invention show, combined with low toxicity, a broad antibacterial spectrum against gram-positive and gram-negative bacteria, in particular against Enterobacteriaceae; above all also against those which are resistant to various antibiotics, such as, for example, penicillins, cephalosporins, aminoglycosides, sulphonamides and tetracyclines.

These useful properties facilitate their use as chemotherapeutic active compounds in medicine and also as substances for the preservation of inorganic and organic materials, in particular of organic materials of all types, for example polymers, lubricants, dyes, fibers, leather, paper and wood, and of foodstuffs and water.

The compounds according to the invention are active against a very wide spectrum of microorganisms. Gram-negative and gram-positive bacteria and bacteria-like microorganisms can be controlled with their aid, and the diseases produced by these pathogens can also be prevented, improved and/or cured.

The compounds according to the invention are particularly active against bacteria and bacteria-like microorganisms. They are therefore particularly well suited in human and veterinary medicine for the prophylaxis and chemotherapy of local and systemic infections which are produced by these pathogens.

For example, local and/or systemic diseases which are caused by the following pathogens or by mixtures of the following pathogens can be treated and/or prevented: gram-positive cocci, for example staphylococci (*Staph. aureus, Staph. epidermidis*) and streptococci (*Strept. agalactiae, Strept. faecalis, Strept. pneumoniae, Strept. pyogenes*); gram-negative cocci (*Neisseria gonorrhoeae*) and also gram-negative rods such as Enterobacteriaceae, for example *Escherichia coli, Haemophilus influenzae*, Citrobacter (*Citrob. freundii, Citrob. divernis*), Salmonella and Shigella; furthermore Klebsiella (*Klebs. pneumoniae, Klebs. oxytoca*), Enterobacter (*Ent. aerogenes, Ent. agglomerans*), Hafnia, Serratia (*Serr. marcescens*), Proteus (*Pr. mirabilis, Pr. rettgeri, Pr. vulgaris*), Providencia, Yersinia, and also the order Acinetobacter. Moreover, the antibacterial spectrum comprises the order Pseudomonas (*Ps. aeruginosa, Ps. maltophilia*) and also strictly anaerobic bacteria such as, for example, *Bacteroides fragilis*, representatives of the order Peptococcus, Peptostreptococcus and also the order Clostridium; furthermore mycoplasma (*M. pneumoniae, M. hominis, M. urealyticum*) and also mycobacteria, for example Mycobacterium tuberculosis.

The above enumeration of pathogens is merely by way of example and in no way to be conceived as limiting. Examples of diseases which may be caused by the said pathogens or mixed infections and which may be prevented, improved or cured by the compounds according to the invention, which may be mentioned are: infectious diseases in humans, such as, for example, otitis, pharyngitis, pneumonia, peritonitis, pyelonephritis, cystitis, endocarditis, systemic infections, bronchitis (acute, chronic), septic infections, diseases of the upper airways, diffuse panbronchiolitis, pulmonary emphysema, dysentery, enteritis, hepatic abscesses, urethritis, prostatitis, epididymitis, gastrointestinal infections, bone and joint infections, cystic fibrosis, skin infections, post-operative wound infections, abscesses, phlegmone, wound infections, infected burns, scalds, infections in the oral region, infections after dental operations, osteomyelitis, septic arthritis, cholecystitis, peritonitis with appendicitis, cholangitis, intra-abdominal abscesses, pancreatitis, sinusitis, mastoiditis, mastitis, tonsillitis, typhus, meningitis and infections of the nervous system, salpingitis, endometritis, genital infections, pelveoperitonitis and eye infections.

In addition to humans, bacterial infections can also be treated in other species. Examples which may be mentioned are:

pig: coli-diarrhoea, enterotoxaemia, sepsis, dysentery, salmonellosis, mastitis-metritis-agalactia syndrome, mastitis;
ruminants (cow, sheep, goat): diarrhoea, sepsis, bronchopneumonia, salmonellosis, pasteurellosis, mycoplasmosis, genital infections;
horse: bronchopneumonias, joint-ill, puerperal and post-puerperal infections, salmonellosis;
dog and cat: bronchopneumonia, diarrhoea, dermatitis, otitis, urinary tract infections, prostatitis;
poultry (hen, turkey, quail, pigeon, ornamental birds and others) mycoplasmosis, *E. coli* infections, chronic airway diseases, salmonellosis, pasteurellosis, psittacosis.

Bacterial diseases in the rearing and keeping of productive and ornamental fish can likewise be treated, the antibacterial spectrum being widened beyond the previously mentioned pathogens to further pathogens such as, for example, Pasteurella, Brucella, Campylobacter, Listeria, Erysipelothrix, Corynebacteria, Borrelia, Treponema, Nocardia, Rickettsia and Yersinia.

The present invention includes pharmaceutical preparations which contain one or more compounds according to the invention or which consist of one or more active compounds according to the invention in addition to non-toxic, inert pharmaceutically suitable excipients and processes for the production of these preparations.

The present invention also includes pharmaceutical preparations in dosage units. This means that the preparations are in the form of individual portions, for example tablets, coated tablets, capsules, pills, suppositories and ampoules, whose active compound content corresponds to a fraction or a multiple of an individual dose. The dosage units may contain, for example, 1, 2, 3 or 4 individual doses or ½, ⅓ or ¼ of an individual dose. An individual dose preferably contains the amount of active compound which is administered in one application and which usually corresponds to a whole, a half, a third or a quarter of a daily dose.

Non-toxic, inert pharmaceutically suitable excipients are taken to mean solid, semi-solid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders and sprays.

Tablets, coated tablets, capsules, pills and granules may contain the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calcium carbonate and sodium carbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i) in addition to the active compound(s).

The tablets, coated tablets, capsules, pills and granules may be provided with the customary coatings and shells containing, if appropriate, opacifying agents and can be so composed that they release the active compound(s), if appropriate with a delay, only or preferably in a certain part of the intestinal tract, it being possible, for example, to use polymeric substances and waxes as embedding materials.

If appropriate, the active compound(s) may also be present in micro-encapsulated form with one or more of the abovementioned excipients.

Suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances in addition to the active compound(s).

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound(s).

Powders and sprays may contain the customary excipients, for example lactose, talc, silica, aluminum hydroxide, calcium silicate and polyamide powder or mixtures of these substances in addition to the active compound(s). Sprays may additionally contain the customary propellants, for example chlorofluorohydrocarbons.

Solutions and emulsions may contain the customary excipients, such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corngerm oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances in addition to the active compound(s).

The said formulation forms may also contain colorants, preservatives and also odor-improving and flavour-improving additives, for example peppermint oil and eucalyptus oil and sweeteners, for example saccharin.

The therapeutically active compounds should preferably be present in the abovementioned pharmaceutical preparations in a concentration of about 0.1 to 99.5, preferably of about 0.5 to 95% by weight, of the total mixture.

The abovementioned pharmaceutical preparations may also contain further pharmaceutical active compounds in addition to the compounds according to the invention.

The preparation of the abovementioned pharmaceutical preparations takes place in a customary manner by known methods, for example by mixing the active compound(s) with the excipient(s).

The preparations mentioned may be used in humans and animals either orally, rectally, parenterally (intravenously, intramuscularly, subcutaneously), intracisternally, intravaginally, intraperitoneally, locally (powder, ointment, drops) and for the therapy of infections in hollow spaces and body cavities. Suitable preparations are injection solutions, solutions and suspensions for oral therapy, gels, pour-on formulations, emulsions, ointments or drops. For local therapy, ophthalmological and dermatological formulations, silver salts and other salts, ear drops, eye ointments, powders or solutions may be used. In animals, the administration may also take place in suitable formulations via the feed or drinking water. Furthermore, gels, powders, tablets, delayed-release tablets, premixes, concentrates, granules, pellets, boli, capsules, aerosols, sprays and inhalants may be used in humans and animals. Furthermore, the compounds according to the invention may be incorporated into other excipient materials such as, for example, Plastics, (plastic chains for local therapy), collagen or bone cement.

In general, it has proved advantageous both in human and veterinary medicine to administer the active compound(s) according to the invention in total amounts of about 0.5 to about 500, preferably 5 to 100 mg/kg of body weight every 24 hours, if appropriate in the form of several individual doses, to attain the desired results. An individual dose preferably contains the active compound(s) according to the invention in amounts of about to about 80, in particular 3 to 30 mg/kg of body weight. However, it may be necessary to depart from the dosages mentioned, depending on the type and the body weight of the subject to be treated, the nature and severity of the disease, the type of preparation and the administration of the medicament and also the time period or interval within which the administration takes place.

Thus in some cases it may be sufficient to manage with less than the abovementioned amount of active compound, whereas in other cases the abovementioned amount of active compound must be exceeded. The optimum dosage required in each case and the type of administration of the active compounds can easily be established by any person skilled in the art on the basis of his expert knowledge.

The new compounds may be given in the customary concentrations and preparations together with the feed or feed preparations or with the drinking water. Infection by gram-negative or gram-positive bacteria can thus be prevented, improved and/or cured and promotion of growth and an improvement in the utilization of the feed can thus be achieved.

The minimum inhibitory concentrations (MIC) were determined by the serial dilution method on iso-sensitest agar (Oxoid). A series of agar plates which contained concentrations of the active compound decreasing in double dilutions in each case were prepared for each test substance. The agar plates were inoculated using a multipoint inoculator (Denley). For the inoculation, overnight cultures of the pathogens were used which were previously diluted in such a way that each inoculation point contained about $10^4$ colony-forming particles. The inoculated agar plates were incubated at 37° C. and the bacterial growth was read off after about 20 hours. The MIC value ($\mu$g/ml) indicates the lowest active compound concentration with which no bacterial growth could be detected with the naked eye.

TABLE 1

[Structure: quinolone core with F at 6-position, R³ at 5, R⁴ at 7, A at 8, R¹ on N-1, COOR² at 3]

| R¹ | R² | R⁴ | R³ | A |
|---|---|---|---|---|
| cyclopropyl | H | diazabicyclic-N | CH₃ | H |
| cyclopropyl | C₂H₅ | diazabicyclic-N | CH₃ | H |
| cyclopropyl | H | diazabicyclic-N | CH₃ | F |
| cyclopropyl | H | diazabicyclic-N | CH₃ | Cl |
| —C₂H₅ | H | diazabicyclic-N | CH₃ | H |
| —C₂H₅ | H | diazabicyclic-N | CH₃ | F |
| 4-F-phenyl | H | diazabicyclic-N | CH₃ | H |
| 2,4-diF-phenyl | H | diazabicyclic-N | CH₃ | H |
| —CH=CH₂ | H | diazabicyclic-N | CH₃ | H |
| HO—CH₂CH₂— | H | diazabicyclic-N | CH₃ | H |
| cyclopropyl | H | diazabicyclic-N | C₂H₅ | H |

TABLE 1-continued
| R¹ | R² | R⁴ | R³ | A |
|---|---|---|---|---|
| 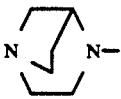 | H |  | $C_2H_5$ | F |
|  | $-C_2H_5$ |  | $CH_3$ | H |
| 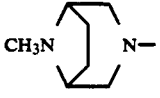 |  |  | $CH_3$ | F |
|  | H |  | $CH_3$ | H |
|  | H | 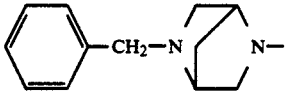 | $C_2H_5$ | H |
|  | H | 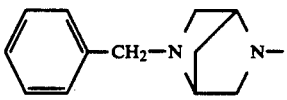 | $CH_3$ | H |
| 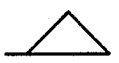 | H | 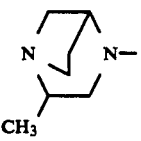 | $CH_3$ | F |
|  | H | 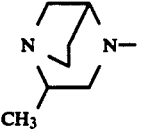 | $CH_3$ | $CH_3$ |
|  | H | 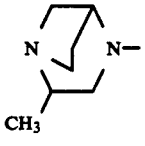 | $CH_3$ | CN |
|  | H | 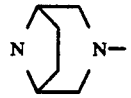 | $C_2H_5$ | F |
|  | H |  | $CH_3$ | Cl |

TABLE 1-continued

| R¹ | R² | R⁴ | R³ | A |
|---|---|---|---|---|
| cyclopropyl | H | benzyl-diazabicyclic-N— | C₂H₅ | Cl |
| F—CH₂—CH₂— | H | diazabicyclic-N— | CH₃ | F |
| cyclopropyl | H | diazabicyclic-N— | C₂H₅ | CH₃ |
| cyclopropyl | H | diazabicyclic-N— | CH₃ | CH₃ |
| cyclopropyl | H | diazabicyclic-N— | CH₃ | NO₂ |
| CH₃O— | H | CH₃N-diazabicyclic-N— | CH₃ | H |
| CH₃—NH— | H | CH₃N-diazabicyclic-N— | CH₃ | F |
| cyclopropyl | H | HN-diazabicyclic-N— | CH₃ | Br |
| cyclopropyl | H | HN-diazabicyclic-N— | CH₃ | CN |
| 2,4-difluorophenyl | H | HN-diazabicyclic-N— | C₂H₅ | CN |
| cyclopropyl | H | oxa-diaza-bicyclic-N— | CH₃ | CH₃ |

TABLE 1-continued

| R¹ | R² | R⁴ | R³ | A |
|---|---|---|---|---|
| cyclopropyl | C₂H₅ | (morpholine-fused pyrrolidine, NH) | CH₃ | H |
| cyclopropyl | H | (thiomorpholine-fused pyrrolidine, NH) | CH₃ | H |
| cyclopropyl | H | (octahydropyrrolo[3,4-b]pyridine, NH) | CH₃ | H |
| C₂H₅ | H | (octahydropyrrolo[3,4-b]pyridine, NH) | CH₃ | H |
| C₂H₅ | H | (octahydropyrrolo[3,4-b]pyridine, NH) | CH₃ | F |
| 4-fluorophenyl | H | (octahydropyrrolo[3,4-b]pyridine, NH) | CH₃ | H |
| 2,4-difluorophenyl | H | (octahydropyrrolo[3,4-b]pyridine, NH) | C₂H₅ | F |
| —CH=CH₂ | H | (octahydropyrrolo[3,4-b]pyridine, NH) | CH₃ | H |
| HO—CH₂CH₂— | H | (methyl-octahydropyrrolo[3,4-b]pyridine, NH) | CH₃ | H |
| cyclopropyl | H | (methyl-octahydropyrrolo[3,4-b]pyridine, NH) | CH₃ | F |

TABLE 1-continued

[Structure: quinolone core with F at 6-position, R³ at 5, R⁴ at 7, A at 8, R¹ on N-1, COOR² at 3-position, 4-oxo]

| R¹ | R² | R⁴ | R³ | A |
|---|---|---|---|---|
| cyclopropyl | H | octahydropyrrolo[3,4-b][1,4]oxazine (NH) | CH₃ | Cl |
| cyclopropyl | —C₂H₅ | octahydropyrrolo[3,4-b][1,4]oxazine (NH) | CH₃ | Cl |
| cyclopropyl | —CH₂-O-C(=O)-O-C(CH₃)= (cyclic carbonate methylidene) | octahydropyrrolo[3,4-b][1,4]oxazine (NH) | CH₃ | F |
| cyclopropyl | H | octahydropyrrolo[3,4-b][1,4]oxazine (NH) | C₂H₅ | H |
| cyclopropyl | H | octahydropyrrolo[3,4-b][1,4]oxazine (NH) | C₂H₅ | F |
| cyclopropyl | H | octahydropyrrolo[3,4-b][1,4]oxazine (NH) | C₂H₅ | Cl |
| cyclopropyl | H | octahydropyrrolo[3,4-b][1,4]oxazine (NH) | CH₃ | CN |
| cyclopropyl | H | octahydropyrrolo[3,4-b][1,4]oxazine (NH) | CH₃ | NO₂ |
| cyclopropyl | H | 2-methyl-octahydropyrrolo[3,4-b][1,4]oxazine (NH) | CH₃ | CH₃ |

TABLE 1-continued
| R¹ | R² | R⁴ | R³ | A |
|---|---|---|---|---|
| 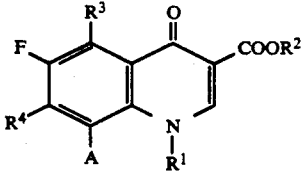 | H |  | C₃H₇ | H |
| 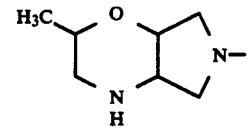 | H |  | CH₃ | F |
| 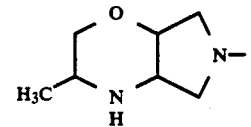 | H |  | CH₃ | Cl |
| F—CH₂CH₂— | H | 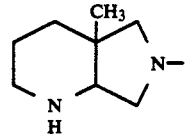 | CH₃ | F |
| 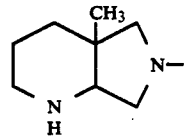 | H |  | CH₃ | H |
| 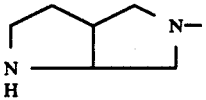 | H |  | CH₃ | F |
| 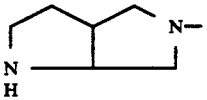 | H |  | CH₃ | Cl |
| CH₃O— | H | 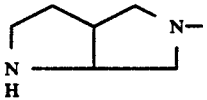 | CH₃ | H |
| CH₃—NH— | H | 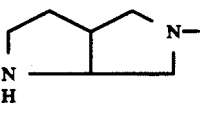 | CH₃ | H |
| 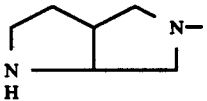 | H |  | CH₃ | H |

TABLE 1-continued
| R¹ | R² | R⁴ | R³ | A |
|---|---|---|---|---|
| 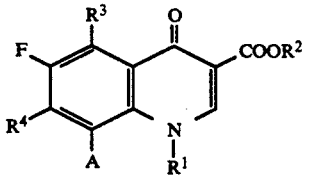 | H |  | CH₃ | F |
| 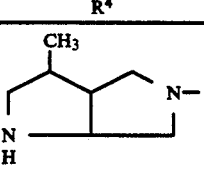 | H |  | CH₃ | Cl |
| 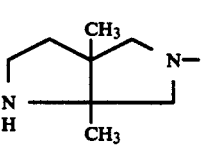 | H |  | CH₃ | F |
| 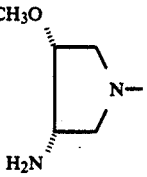 | H |  | CH₃ | H |
| 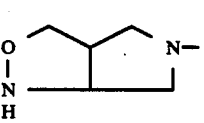 | H |  | CH₃ | F |
| 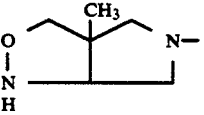 | H |  | CH₃ | H |
| 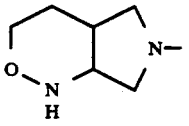 | H |  | CH₃ | F |
| 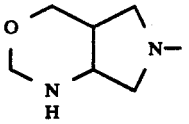 | H |  | CH₃ | CH₃ |
| 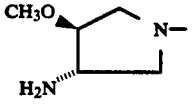 | H |  | CH₃ | F |
|  | H | 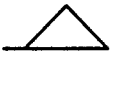 | C₂H₅ | F |

TABLE 1-continued
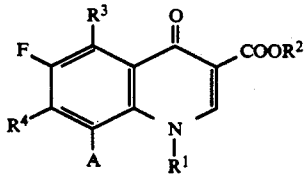
| R¹ | R² | R⁴ | R³ | A |
|---|---|---|---|---|
| —C₂H₅ | H | 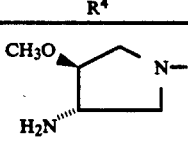 | C₂H₅ | Cl |
|  | C₂H₅ |  | C₂H₅ | Cl |
|  | H |  | CH₃ | F |
|  | CH₃ | 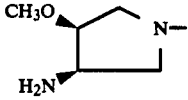 | CH₃ | Cl |
| —C₂H₅ | H | 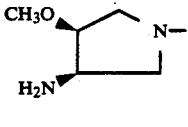 | CH₃ | F |
|  | H |  | CH₃ | F |
|  | H |  | CH₃ | F |
|  | H | 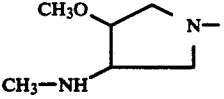 | CH₃ | H |
|  | H | 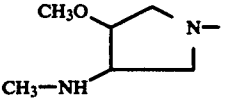 | CH₃ | F |
|  | H | 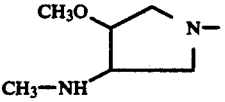 | C₂H₅ | F |
|  | H | 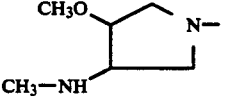 | C₂H₅ | Cl |

TABLE 1-continued

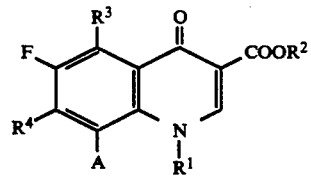

| R¹ | R² | R⁴ | R³ | A |
|---|---|---|---|---|
| cyclopropyl | H | 3-(dimethylamino)-4-methoxypyrrolidin-1-yl | CH₃ | F |
| cyclopropyl | H | 3-(dimethylamino)-4-methoxypyrrolidin-1-yl | n-C₃H₇ | H |
| cyclopropyl | H | 3-(methylaminomethyl)-3-hydroxypyrrolidin-1-yl | CH₃ | H |
| " | H | " | CH₃ | F |
| " | H | " | CH₃ | Cl |
| " | C₂H₅ | " | CH₃ | F |
| " | —CH₂—C(CH₃)=C(O)—O—C(=O)—O— (cyclic carbonate) | " | CH₃ | F |
| " | H | " | CH₃ | CN |
| C₂H₅— | H | " | CH₃ | F |
| 2,4-difluorophenyl | H | 3-(methylaminomethyl)-3-hydroxypyrrolidin-1-yl | CH₃ | F |
| cyclopropyl | H | 3-(ethylaminomethyl)-3-hydroxypyrrolidin-1-yl | CH₃ | H |
| " | H | " | CH₃ | F |
| " | H | " | C₂H₅ | F |
| C₂H₅— | H | " | CH₃ | H |
| 4-fluorophenyl | H | " | CH₃ | H |
| cyclopropyl | C₂H₅ | " | CH₃ | F |

TABLE 1-continued
| R¹ | R² | R⁴ | R³ | A |
|---|---|---|---|---|
| 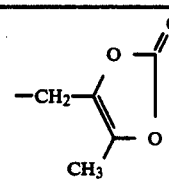 | 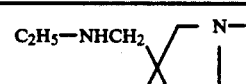 | 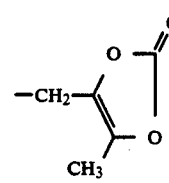 | CH₃ | H |
| " | C₂H₅ | " | CH₃ | F |
| " | 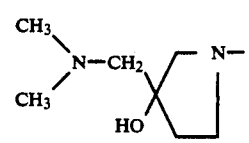 | " | CH₃ | F |
| " | H | 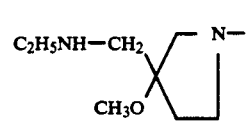 | CH₃ | H |
| " | H | " | CH₃ | F |
| " | H | " | C₂H₅ | F |
| " | H | " | CH₃ | Cl |
| " | H |  | CH₃ | H |
| 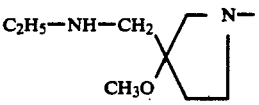 | H | 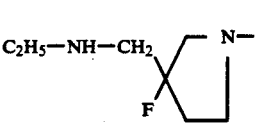 | CH₃ | F |
| " | H | " | CH₃ | Cl |
| " | H | 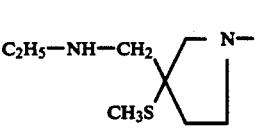 | CH₃ | F |
| " | H | " | C₂H₅ | F |
| " | H | " | CH₃ | Cl |
| " | H | " | CH₃ | CN |
| " | H |  | CH₃ | H |
| " | H | " | CH₃ | F |
| 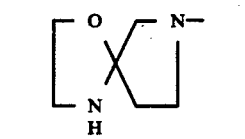 | H | (spiro morpholine-pyrrolidine structure) | CH₃ | H |

TABLE 1-continued

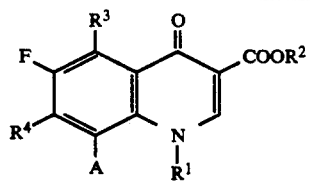

| R¹ | R² | R⁴ | R³ | A |
|---|---|---|---|---|
| " | H | " | CH₃ | F |
| " | H | " | C₂H₅ | F |
| " | H | " | n-C₃H₇ | F |
| " | H | " | CH₃ | Cl |
| " | H | H₂N—CH₂–C(OH)(CH₂–)–N— (with pendant CH₂ forming ring) | CH₃ | F |
| " | H | " | CH₃ | NO₂ |
| " | H | " | CH₃ | CN |
| " | H | H₂N—CH₂–C(OH)(–)–N— (piperidine) | CH₃ | F |
| " | H | " | CH₃ | H |
| " | H | " | CH₃ | Cl |
| cyclopropyl | H | (CH₃)₂N—CH₂–C(OH)(–)–N— (piperidine) | CH₃ | H |
| " | H | " | CH₃ | F |

EXAMPLE A

7-Chloro-1-cyclopropyl-6,8-difluoro-1,4-dihydro-5-methyl-4-oxo-3-quinolinecarboxylic acid a)

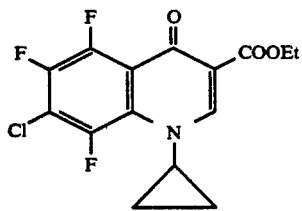

8.0 g of 1-cyclopropyl-5,6,7,8-tetrafluoro-1,4-dihydro-4-oxo-3-quinolinecarboxylic acid and 7.9 ml of thionyl chloride are boiled until gas no longer escapes. The mixture is then concentrated in vacuo. 50 ml of ethanol are added to the residue and the mixture is boiled for two hours. It is then cooled to room temperature and the solid precipitated is isolated.

Yield: 8.6 g of ethyl 7-chloro-1-cyclopropyl-5,6,8-trifluoro-1,4-dihydro-4-oxo-3-quinolinecarboxylate Melting point: 166°–168° b)

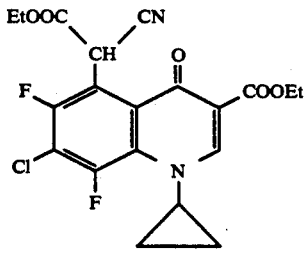

1.6 ml (0.015 mol) of ethyl cyanoacetate are initially introduced into 50 ml of absolute dioxane and 0.58 g of sodium hydride (as the 80% strength material) are added at 20° C. After 30 minutes, 3.45 g (0.01 mol) of substance from a) are added. The mixture is then boiled under reflux for 6 hours. After cooling to 20°, the mixture is diluted with water and rendered acidic with hydrochloric acid. The solid is isolated, dried and recrystallized from isopropanol.

Yield: 2.3 g of ethyl 7-chloro-5-(cyano-ethoxycarbonylmethyl)-1-cyclopropyl-6,8-difluoro-1,4-dihydro-4-oxo-3-quinolinecarboxylate Melting point: 156°–57°

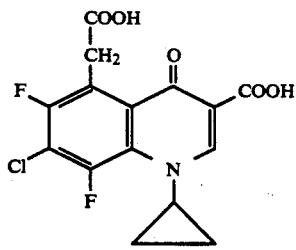

2.3 g of substance from b) are heated at 140° for hours together with 6 ml of acetic acid, 5 ml of water and 0.5 ml of sulphuric acid. The mixture is cooled to 20° and diluted with water. The solid is isolated, washed with water and dried.

Yield: 1.6 g of 5-carboxymethyl-7-chloro-1-cyclopropyl-6,8-difluoro-1,4-dihydro-4-oxo-3-quinolinecarboxylic acid

|  | Analysis: | | | |
| --- | --- | --- | --- | --- |
|  | C | H | N | Cl |
| calculated: | 50.3 | 3.0 | 3.9 | 9.9 |
| found: | 50.5 | 3.2 | 3.7 | 10.0 |
|  | 50.6 | 3.2 | 3.8 | 9.9 |

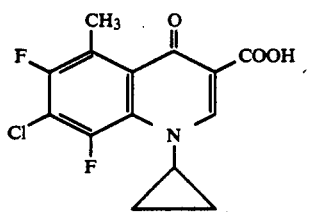

d)

1.0 g (2.8 mmol) of substance from c) and 0.9 g (8.4 mmol) of 1,4-diazabicyclo[2.2.2]octane are heated at 140° for 3 hours in 20 ml of dimethyl sulphoxide. The solvent is then removed in a high vacuum and the residue is chromatographed on silica gel (eluent: methylene chloride/methanol 99/1).

Yield: 0.2 g of 7-chloro-1-cyclopropyl-6,8-difluoro-1,4-dihydro-5-methyl-4-oxo-3-quinolinecarboxylic acid Melting point: 195°–7°

EXAMPLE 1

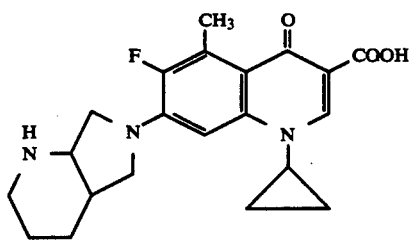

0.56 g (2 mmol) of 1-cyclopropyl-6,7-difluoro-1,4-dihydro-5-methyl-4-oxo-3-quinolinecarboxylicacid are heated at 140° C. for 2 hours with 0.384 g (3 mmol) of 2,8-diazabicyclo[4.3.0]nonane and 0.672 g (6 mmol) of 1,4-diazabicyclo[2.2.2]octane in 3.5 ml of dimethyl sulphoxide. After cooling, the DMSO is removed in a high vacuum. The residue is taken up using acetonitrile.

c) The solid is separated off, washed with acetonitrile and dried at 60°–80°.

Yield: 0.7 g of 1-cyclopropyl-7-(2,8-diazabicyclo[4.3.0]non-8-yl)-6-fluoro-1,4-dihydro-5-methyl-4-oxo-3-quinolinecarboxylate Melting point: 174°–6° with decomposition

EXAMPLE 2

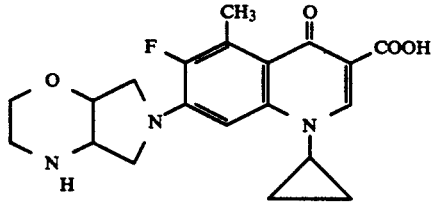

0.28 g (1 mmol) of 1-cyclopropyl-6,7-difluoro-1,4-dihydro-5-methyl-4-oxo-3-quinolinecarboxylate are heated at 140° C. for 2 hours with 0.19 g (1.5 mmol) of 2-oxa-5,8-diazabicyclo[4.3.0]nonane and 0.34 g (3 mmol) of 1,4-diazabicyclo-[2.2.2.]octane in 3.5 ml of dimethyl sulphoxide. The dimethyl sulphoxide is distilled off in a high vacuum. The residue is stirred with acetonitrile and the solid is isolated.

Yield: 0.27 g of 1-cyclopropyl-6-fluoro-1,4-dihydro-5-methyl-7-(2-oxa-5,8-diazabicyclo[4.3.0]non-8-yl)-4-oxo-3-quinolinecarboxylic acid Melting point: 273°–5°

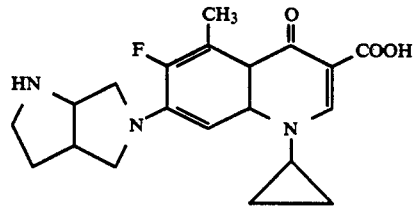

0.14 g (0.5 mmol) of 1-cyclopropyl-6,7-difluoro-1,4-dihydro-5-methyl-4-oxo-3-quinolinecarboxylicacidare heated at 140° for 2 hours with 0.084 g (0.75 mmol) of 2,7-diazabicyclo[3.3.0]octane and 0.17 g (1.5 mmol) of 1,4-diazabicyclo[2.2.2]octane in 3.5 ml of dimethyl sulphoxide. Dimethyl sulphoxide is then distilled off in a high vacuum. Acetonitrile is added to the residue, whereupon a solid forms.

Yield: 0.15 g of 1-cyclopropyl-7-(2,7-diazabicyclo-[3.3.0]oct-7-yl)-6-fluoro-1,4-dihydro-5-methyl-4-oxo-3-quinolinecarboxylic acid Melting point: 232°–4° with decomposition

EXAMPLE 4

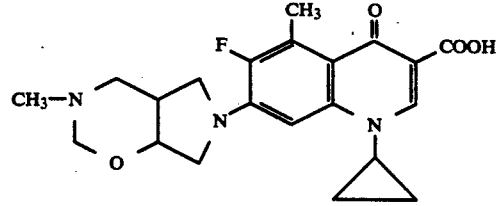

0.28 g (1 mmol) of 1-cyclopropyl-6,7-difluoro-1,4-dihydro-5-methyl-4-oxo-3-quinolinecarboxylicacidare heated to 140° for 2 hours with 0.213 g (1.5 mmol) of 5-methyl-3-oxo-5,8-diazabicyclo[4.3.0]nonane and 0.34 g (3 mmol) of 1,4-diazabicyclo[2.2.2]octane in 3.5 ml of dimethyl sulphoxide. The solvent is then removed in a high vacuum. After stirring the residue with acetonitrile, 0.22 g of 1-cyclopropyl-6-fluoro-1,4-dihydro-5-methyl-7-(5-methyl-3-oxo-5,8-diazabicyclo[4.3.0]non-8-yl)-4-oxo-3-quinolinecarboxylic acid are obtained.

Melting point: 208°-10° with decomposition

EXAMPLE 5

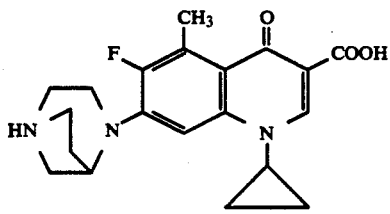

0.28 g (1 mmol) of I-cyclopropyl-6,7-difluoro-1,4-dihydro-5-methyl-4-oxo-3-quinolinecarboxylicacidare heated at 140° for 2 hours with 0.17 g (1.5 mmol) of 1,4-diazabicyclo[3.2.1]octane and 0.34 g (3 mmol) of 1,4-diazabicyclo[2.2.2]octane in 3.5 ml of dimethyl sulphoxide. After removing the solvent in a high vacuum, the residue is stirred with acetonitrile and the solid is isolated.

Yield: 0.24 g of 1-cyclopropyl-7-(1,4-diazabicyclo-[3.2.1]oct-4-yl)-6-fluoro-1,4-dihydro-5-methyl-4-oxo-3-quinolinecarboxylic acid Melting point: 274°-76° with decomposition

EXAMPLE B

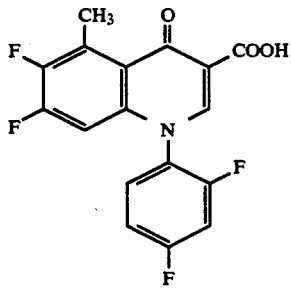

6,7-Difluoro-1-(2,4-difluoro-phenyl)-1,4-dihydro-5-methyl-4-oxo-3-quinolonecarboxylic acid

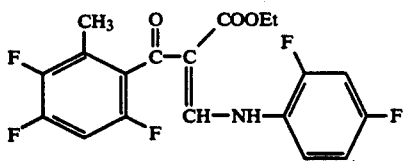

21 g of ethyl 3-ethoxy-2-(2,4,5-trifluoro-6-methyl-benzoyl)acrylate are initially introduced into 55 ml of ethanol. 9.4 g of 2,4-difluoroaniline are added dropwise with cooling. The mixture is then stirred at 25° C. for one hour. 55 ml of water are then added and the solid which precipitates is isolated.

Yield: 25 g of ethyl 3-(2,4-difluorophenylamino)-2-(2,4,5-trifluoro-6-methyl-benzoyl)-acrylate Melting point 109°-10° C.

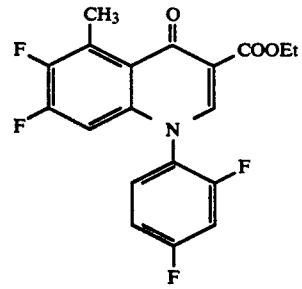

12.5 g of substance from a) and 5.1 g of potassium carbonate are heated at 140° C. for 4 hours in 60 ml of dimethylformamide. After cooling to room temperature, the mixture is diluted with water. The solid which precipitates is isolated and dried.

Yield: 11.3 g of ethyl 6,7-difluoro-1-(2,4-difluorophenyl)-1,4-dihydro-5-methyl-4-oxo-3-quinolinecarboxylate Melting point: 157°-9°

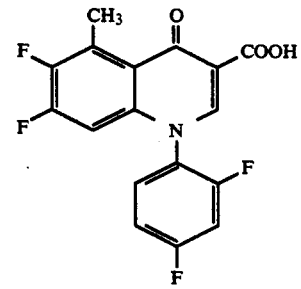

11.2 g of substance from b), 70 ml of acetic acid, 70 ml of water and 3.5 ml of sulphuric acid are heated at 140° C. for 4 hours. After cooling to room temperature, the mixture is diluted with water. The solid is isolated and dried. 10.3 g of the title compound are obtained. Melting point: 277°-8° C.

EXAMPLE 6

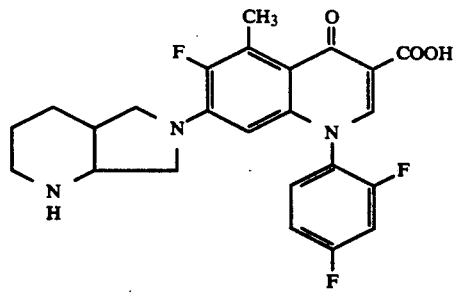

0.6 g of substance from Example B, 0.57 g of 1,4-diazabicyclo[2.2.2]-octane and 0.25 g of 2,8-diazabicyclo[4.3.0]-nonane are stirred at room temperature in 6 ml of dimethyl sulphoxide until starting material is no longer detectable in the thin layer chromatogram. The mixture is then concentrated in vacuo. Water is added to the residue and the solid is isolated.

Yield: 0.6 g of 7-(2,8-diazabicyclo[4.3.0]non-8-yl)-1-(2,4-difluorophenyl)-6-fluoro-1,4-dihydro-5-methyl-4-oxo-3-quinolinecarboxylic acid.

Melting point: 247°-8° C.

EXAMPLE 7

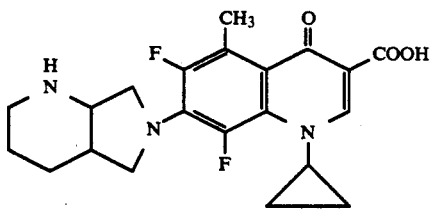

1.1 g (3.5 mmol) of the compound according to Example A d), 0.59 (5.3 mmol) 2,8-diazabicyclo[4.3.0]nonane and 1.58 g (10.5 mmol) 1,4-diazabicyclo[2.2.2]octane are dissolved in 20 mol dimethylsulfoxide and are heated to 140° C. for three hours. Subsequently, the reaction mixture is cooled down to room temperature and the solvent is removed in vacuo. The residue is dissolved in water and the pH is adjusted to 7. The precipitate is isolated by filtration, washed with water and dried.

1.0 g 1-cyclopropyl-7-(2,8-diazabicyclo[4.3.0]non-8-yl)-6,8-difluoro-1,4-dihydro-5-methyl-4-oxo-3-quinolone carboxylic acid is obtained.

Melting point: 185°-7° C.

It will be understood that the specification and examples are illustrative but not limitative of the present invention and that other embodiments within the spirit and scope of the invention will suggest themselves to those skilled in the art.

We claim:

1. The compound 1-cyclopropyl-7-(2,7-diazabicyclo[3.3.0]oct-7-yl)-6-fluoro-1,4-dihydro-5-methyl-4-oxo-3-quinolinecarboxylic acid of the formula

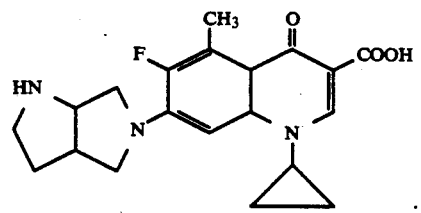

2. An antibacterially active composition comprising an antibacterially effective amount of a compound, hydrate or salt thereof according to claim 1 and a diluent.

3. A method of combating bacteria which comprises applying to a host in need thereof an antibacterially effective amount of a compound, hydrate or salt thereof according to claim 1.

* * * * *

UNITED STATES PATENT AND TRADEMARK OFFICE
CERTIFICATE OF CORRECTION

PATENT NO. : 5,140,033

DATED : August 18, 1992

INVENTOR(S) : Schriewer et al.

It is certified that error appears in the above-identified patent and that said Letters Patent is hereby corrected as shown below:

Title Page    [75] Inventors: After " Thomas Schenke, " insert -- Bergisch --

Title Page    [63] Delete " now Defensive Publication No. "

Signed and Sealed this

Twenty-eighth Day of December, 1993

Attest:

BRUCE LEHMAN

*Attesting Officer*      *Commissioner of Patents and Trademarks*